(12) United States Patent
Lai et al.

(10) Patent No.: US 6,429,223 B1
(45) Date of Patent: Aug. 6, 2002

(54) MODIFIED FORMS OF PHARMACOLOGICALLY ACTIVE AGENTS AND USES THEREFOR

(75) Inventors: Ching-San Lai, Encinitas; Tingmin Wang, San Marcos, both of CA (US)

(73) Assignee: Medinox, Inc., San Diego, CA (US)

( * ) Notice: Subject to any disclaimer, the term of this patent is extended or adjusted under 35 U.S.C. 154(b) by 0 days.

(21) Appl. No.: 09/715,767

(22) Filed: Nov. 17, 2000

Related U.S. Application Data

(63) Continuation-in-part of application No. 09/602,688, filed on Jun. 23, 2000.
(51) Int. Cl.[7] ...................... A61K 31/48; A61K 31/405; A61K 31/255; A61K 31/40; A61K 37/34
(52) U.S. Cl. ................ 514/411; 514/415; 514/424; 514/517; 514/532; 514/533; 514/534
(58) Field of Search .................. 548/366.7; 514/424, 514/411, 415, 517, 532, 533, 534

(56) References Cited

U.S. PATENT DOCUMENTS 6,177,466 B1 * 1/2001 Sakaki et al. ............... 514/538

OTHER PUBLICATIONS

Onoe, Yoshiko, et al., "IL–13 and IL–4 Inhibit Bone Resorption by Suppressing Cyclooxygenase–2–Dependent Prostaglandin Synthesis in Osteoblasts," *J. Immunol.* 156:758–764 (1996).
Mitchell, Jane A., et al., "Selectivity of Nonsteroidal Anti-inflammatory Drugs as Inhibitors of Constitutive And Inducible Cyclooxygenase," *Proc. Natl. Acad. Sci. USA* 90:11693–11697 (1994).
Glaser, Keith, et al., "Etodolac Selectively Inhibits Human Prostaglandin G/H Synthase 2 (PGHS–2)) Versus Human PGHS–1," *European J. Pharm.* 281:107–111 (1995).
Carson, Jeffrey L., et al., "The Relative Gastrointestinal Toxicity of the Nonsteroidal Anti–inflammatory Drugs," *Arch Intern Med* 147:1054–1059 (1987).
Slater, Donna M., et al., "Expression of Cyclooxygenase Types 1 and 2 in Human Fetal Membranes at Term," *Am. J. Obstet. Gynecol.* 172:77–82 (1995).
Graham, David Y., et al., "Nonsteroidal Anti–inflammatory Effect of Sulindac Sulfoxide and Sulfide on Gastric Mucosa," *Clin. Pharmacol. Ther.* 38:65–70 (1985).
Bjarnason, Ingvar, et al., "Side Effects of Nonsteroidal Anti–inflammatory Drugs on the Small and Large Intestine in Humans," *Gastroenterology* 104:1832–1847 (1993).
Kargman. Stacia, et al., "Characterization of Prostaglandin G/H Synthase 1 and 2 in Rat, Dog, Monkey, and Human Gastrointestinal Tracts," *Gastroenterology* 111:445:454 (1996).
Wallace, John L., "Nonsteroidal Anti–inflammatory Drugs and Gastroenteropathy: The Second Hundred Years" *Gastroenterology* 112:1000–1016 (1997).
Kaplan–Machlis, Barbara, et al., "The Cyclooxygenase–2 Inhibitors: Safety and Effectiveness," *Annals of Pharmacotherapy* 33:979–988 (1999).
Soll, Andrew H., et al., "Nonsteroidal Anti–Inflammatory Drugs and Peptic Ulcer Disease," *Annals of Internal Medicine* 114:307–319 (1991).
Meade, Elizabeth A., et al., "Differential Inhibition of Prostaglandin Endoperoxide Synthase (Cyclooxygenase) Isozymes by Aspirin and Other Non–steroidal Anti–inflammatory Drugs," *J.Biol. Chem.* 268(9):6610–6614 (1993).

* cited by examiner

*Primary Examiner*—Floyd D. Higel
(74) *Attorney, Agent, or Firm*—Stephen E. Reiter; Kevin J. Forrestal; Foley & Lardner

(57) ABSTRACT

In accordance with the present invention, there are provided modified forms of nonsteroidal anti-inflammatory drugs (NSAIDs). Modified NSAIDs according to the invention provide a new class of anti-inflammatory agent which provide the therapeutic benefits of NSAIDs while causing a much lower incidence of side-effects then typically observed with such agents.

25 Claims, 4 Drawing Sheets

MODIFIED FORMS OF PHARMACOLOGICALLY ACTIVE AGENTS AND USES THEREFOR

This application is a continuation-in-part of U.S. Ser. No. 09/602,688, filed Jun. 23, 2000.

FIELD OF THE INVENTION

The present invention relates to novel forms of pharmacologically active agents, and methods for the preparation and use thereof. In a particular aspect of the invention, methods are provided for treating pathological conditions with a modified form of one or more pharmacologically active agents, thereby reducing the occurrence of side-effects caused thereby.

BACKGROUND OF THE INVENTION

Despite the advent of modem pharmaceutical technology, many drugs still possess untoward toxicities which often limit the therapeutic potential thereof. For example, although nonsteroid antiinflammatory drugs (NSAIDs) are a class of compounds which are widely used for the treatment of inflammation, pain and fever, NSAIDs (e.g., naproxen, aspirin, ibuprofen and ketoprofen) can cause gastrointestinal ulcers, a side effect that remains the major limitation to the use of NSAIDs (see, for example, J. L. Wallace, in Gastroenterol. 112:10001016 (1997); A. H. Soll et al., in Ann Intern Med. 114:307319 (1991); and J. Bjarnason et al., in Gastroenterol. 104:18321847 (1993)).

There are two major ulcerogenic effects of NSAIDs: (1) irritant effects on the epithelium of the gastrointestinal tract and (2) suppression of gastrointestinal prostaglandin synthesis. In recent years, numerous strategies have been attempted to design and develop new NSAIDs that reduce the damage to the gastrointestinal tract. These efforts, however, have largely been unsuccessful. For example, enteric coating or slow release formulations designed to reduce the topical irritant properties of NSAIDs have been shown to be ineffective in terms of reducing the incidence of clinically significant side effects, including perforation and bleeding (see, for example, D. Y. Graham et al., in Clin. Pharmacol. Ther. 38:6570 (1985); and J. L. Carson, et al., in Arch. Intern. Med., 147:10541059 (1987)).

It is well recognized that aspirin and other NSAIDs exert their pharmacological effects through the non-selective inhibition of cyclooxygenase (COX) enzymes, thereby blocking prostaglandin synthesis (see, for example, J. R. Van in Nature, 231:232235 (1971)). There are two types of COX enzymes, namely COX1 and COX2. COX1 is expressed constitutively in many tissues, including the stomach, kidney, and platelets, whereas COX2 is expressed only at the site of inflammation (see, for example, S. Kargan et al. in Gastroenterol., 111:445454 (1996)). The prostagladins derived from COX1 are responsible for many of the physiological effects, including maintenance of gastric mucosal integrity.

Many attempts have been made to develop NSAIDs that only inhibit COX2, without impacting the activity of COX1 (see, for example, J. A. Mitchell et al., in Proc. Natl. Acad. Sci. USA 90:1169311697 (1993); and E. A. Meade et al., in J. Biol. Chem., 268:66106614 (1993)). There are several NSAIDs presently on the market (e.g., rofecoxib and celecoxib) that show marked selectivity for COX2 (see, for example, E. A. Meade, supra.; K. Glaser et al., in Eur. J. Pharmacol. 281:107111 (1995) and Kaplan-Machlis, B., and Klostermeyer, B S in Ann Pharmacother. 33:979–88, (1999)). These drugs appear to have reduced gastrointestinal toxicity relative to other NSAIDs on the market.

On the basis of encouraging clinical as well as experimental data, the development of highly selective COX2 inhibitors appears to be a sound strategy to develop a new generation of antiinflammatory drugs. However, the physiological functions of COX1 and COX2 are not always well defined. Thus, there is a possibility that prostagladins produced as a result of COX1 expression may also contribute to inflammation, pain and fever. On the other hand, prostagladins produced by COX2 have been shown to play important physiological functions, including the initiation and maintenance of labor and in the regulation of bone resorption (see, for example, D. M. Slater et al., in Am. J. Obstet. Gynecol., 172:7782 (1995); and Y. Onoe et al., in J. Immunol. 156:758764 (1996)), thus inhibition of this pathway may not always be beneficial. Considering these points, highly selective COX2 inhibitors may produce additional side effects above and beyond those observed with standard NSAIDs, therefore such inhibitors may not be highly desirable.

Accordingly, there is still a need in the art for modified forms of NSAIDs which cause a reduced incidence of side-effects, relative to the incidence of side-effects caused by such pharmacologically active agents in unmodified form.

BRIEF DESCRIPTION OF THE INVENTION

In accordance with the present invention, there is provided a new class of modified NSAIDs which cause a much lower incidence of side-effects than are typically observed with unmodified NSAIDs due to the protective effects imparted by modifying the NSAIDs as described herein.

There are a number of advantages provided by modified NSAIDs according to the invention including one or more of the following:

(i) reduced irritant effects (e.g., contact irritation) of NSAIDs, (ii) enhanced tissue delivery of the drug as a result of a decrease in net charges on the molecule, particularly for acidic NSAIDs such as naproxen, aspirin, diclofenac and ibuprofen, thereby reducing the quantity of material which must be delivered to achieve an effective dosage, and (iii) reduction in the maximum concentration ($C_{max}$) achieved upon administration to a subject relative to the unmodified NSAID, while maintaining a therapeutically effective concentration of the NSAID in plasma of the subject.

In accordance with the present invention, cleavage of the modified NSAIDs described herein from the modified group appended thereto releases the pharmaceutically active agent.

DETAILED DESCRIPTION OF THE INVENTION

Figure 1:
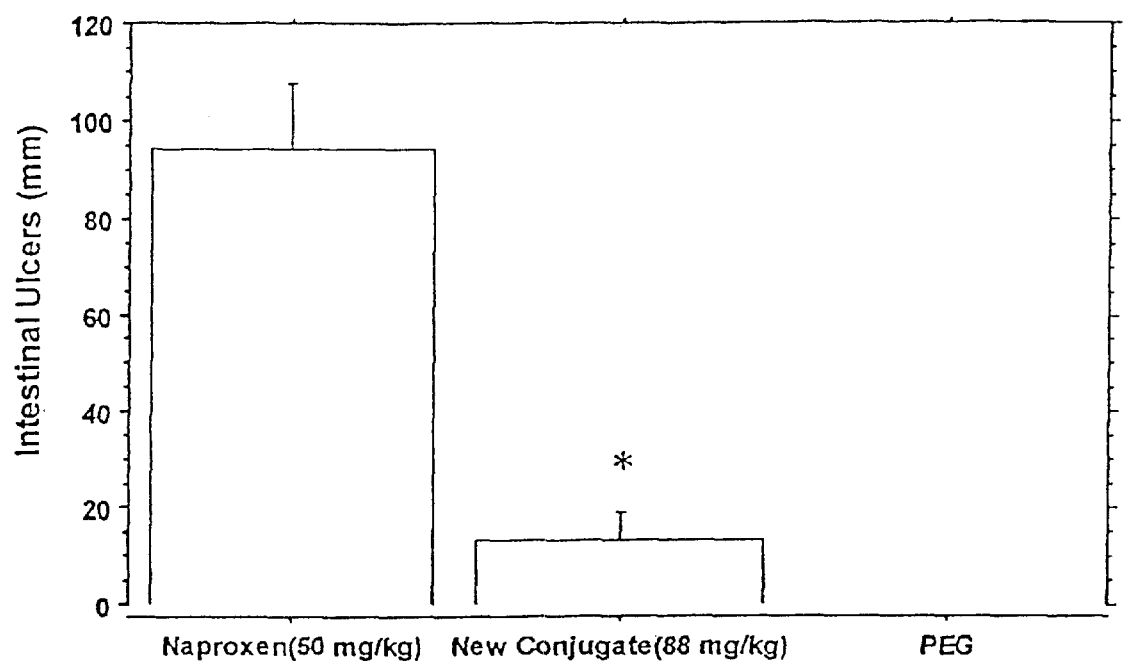
FIG. 1 illustrates the total length of intestinal ulcers measured after three daily doses of NSAID in unfasted male Sprague-Dawley rats (150–200 g) treated with vehicle, naproxen, or equimolar invention composition (compound 19). *$P<0.05$ by unpaired t-test.

In accordance with the present invention, there are provided compounds comprising a modified NSAID, wherein the NSAID is covalently attached either directly or through a linker molecule to a sulfur-containing functional group containing an optionally substituted hydrocarbyl moiety. Exemplary invention compounds have the structure:

wherein:
X=a non-steroidal anti-inflammatory drug (NSAID),
L=an optional linker/spacer, and
Z=a sulfur-containing functional group containing an optionally substituted hydrocarbyl moiety.

NSAIDs contemplated for modification in accordance with the present invention include acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (lodine), fenoprofen calcium (nalfon), flurbiprofen (ansaid), indomethacin (indocin, indometh, others), ketoprofen (orudis, oruvail), carprofen, indoprofen, ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolmetin (tolectin), meloxicam, nabumetone, naproxen, lornoxicam, nimesulide, indoprofen, remifenzone, salsalate, tiaprofenic acid, flosulide, and the like. Presently preferred NSAIDs employed in the practice of the invention include naproxen, aspirin, ibuprofen, flurbiprofen, indomethacin, ketoprofen, carprofen, and the like. When the NSAID is aspirin, the sulfur-containing functional groups —$CH_2S(O)_2CH_3$, —$CH_2S(O)CH_3$, and —$SCH_3$ are not presently preferred.

Invention compounds can be readily prepared in a variety of ways either by direct reaction of NSAIDs with the sulfur-containing functional group or indirectly through a suitable linker molecule.

The components of invention compositions are directly or indirectly covalently attached employing a variety of linkages (including an optional linker), e.g., ester linkages, disulfide linkages, amide linkages, immine linkages, enamine linkages, ether linkages, thioether linkages, imide linkages, sulfate ester linkages, sulfonate ester linkages, sulfone linkages, sulfonamide linkages, phosphate ester linkages, carbonate linkages, O-glycosidic linkages, S-glycosidic linkages, and the like. Such linkages can be accomplished using standard synthetic techniques as are well known by those of skill in the art, either by direct reaction of the starting materials, or by incorporating a suitable functional group on the starting material, followed by coupling of the reactants.

When the pharmacologically active agents contemplated for use herein contain suitable functionality thereon, e.g., hydroxy, amino, carboxy, and the like, invention modified NSAIDs can be prepared by direct linkage between the two agents. Alternatively, the NSAIDs can be functionalized so as to facilitate linkage between the two agents. When present, linker/spacer L has the following structure:

wherein:
R is optional, and when present is alkylene, substituted alkylene, cycloalkylene, substituted cycloalkylene, heterocyclic, substituted heterocyclic, oxyalkylene, substituted oxyalkylene, alkenylene, substituted alkenylene, arylene, substituted arylene, alkarylene, substituted alkarylene, aralkylene or substituted aralkylene, and W is ester, reverse ester, thioester, reverse thioester, amide, reverse amide, phosphate, phosphonate, imine, enamine, or the like.

Functional groups contemplated by the present invention are sulfur-based. Examples of suitable sulfur-containing functional groups include sulfonate, reverse sulfonate, sulfonamide, reverse sulfonamide, sulfone, sulfinate, reverse sulfinate, and the like. In a particular aspect of the invention, the sulfur-based moiety is sulfonate or reverse sulfonate. In a particularly preferred aspect of the invention, the sulfonate is an optionally substituted aromatic sulfonate such as tosylate or brosylate.

Other preferred sulfur-based functional groups contemplated by the present invention include sulfones. Preferably, the sulfone is an optionally substituted alkyl or aromatic sulfone.

In one aspect of the invention, Z may have the following structure:

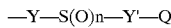

wherein:
each of Y and Y' are optionally present, and when present are independantly —O— or —NR'—, wherein R' is H or an optionally substituted hydrocarbyl moiety;
n is 1 or 2, and
Q is H or an optionally substituted hydrocarbyl moiety.

As employed herein, "hydrocarbyl" embraces alkyl, substituted alkyl, oxyalkyl, substituted oxyalkyl, cycloalkyl, substituted cycloalkyl, alkenyl, substituted alkenyl, alkynyl, substituted alkynyl, monocyclic heterocyclic, substituted monocyclic heterocyclic, monocyclic aromatic, monosubstituted monocyclic aromatic, or the like.

As employed herein, "alkyl" refers to hydrocarbyl radicals having 1 up to 20 carbon atoms, preferably 2–10 carbon atoms; and "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, C(O)H, acyl, oxyacyl, carboxyl, carbamate, sulfonyl, sulfonamide, sulfuryl, and the like.

As employed herein, "oxyalkyl" refers to the moiety —O-alkyl-, wherein alkyl is as defined above, and "substituted oxyalkyl" refers to oxyalkyl groups further bearing one or more substituents as set forth above.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynylene groups further bearing one or more substituents as set forth above.

As employed herein, "monocyclic aromatic" refers to aromatic groups having in the range of 5 up to 7 carbon atoms and "monosubstituted monocyclic aromatic" refers to aromatic groups further bearing one of the substituents set forth above.

As employed herein, "alkylene" refers to divalent hydrocarbyl radicals having 1 up to 20 carbon atoms, preferably 2–10 carbon atoms; and "substituted alkylene" comprises alkylene groups further bearing one or more substituents as set forth above.

As employed herein, "cycloalkylene" refers to cyclic ring-containing groups containing in the range of about 3 up to 8 carbon atoms, and "substituted cycloalkylene" refers to cycloalkylene groups further bearing one or more substituents as set forth above.

As employed herein, "oxyalkylene" refers to the moiety —O-alkylene-, wherein alkylene is as defined above, and "substituted oxyalkylene" refers to oxyalkylene groups further bearing one or more substituents as set forth above.

As employed herein, "alkenylene" refers to divalent, straight or branched chain hydrocarbyl groups having at least one carbon-carbon double bond, and having in the range of about 2 up to 12 carbon atoms, and "substituted alkenylene" refers to alkenylene groups further bearing one or more substituents as set forth above.

As employed herein, "alkynylene" refers to divalent straight or branched chain hydrocarbyl groups having at least one carbon-carbon triple bond, and having in the range of about 2 up to 12 carbon atoms, and "substituted alkynylene" refers to alkynylene groups further bearing one or more substituents as set forth above.

As employed herein, "arylene" refers to divalent aromatic groups having in the range of 6 up to 14 carbon atoms and "substituted arylene" refers to arylene groups further bearing one or more substituents as set forth above.

As employed herein, "alkylarylene" refers to alkyl-substituted arylene groups and "substituted alkylarylene" refers to alkylarylene groups further bearing one or more substituents as set forth above.

As employed herein, "arylalkylene" refers to aryl-substituted alkylene groups and "substituted arylalkylene" refers to arylalkylene groups further bearing one or more substituents as set forth above.

As employed herein, "arylalkenylene" refers to aryl-substituted alkenylene groups and "substituted arylalkenylene" refers to arylalkenylene groups further bearing one or more substituents as set forth above.

As employed herein, "arylalkynylene" refers to aryl-substituted alkynylene groups and "substituted arylalkynylene" refers to arylalkynylene groups further bearing one or more substituents as set forth above.

Diseases and conditions contemplated for treatment in accordance with the present invention include inflammatory and infectious diseases, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., ulcerative colitis or Crohn's disease), diabetes, arthritis (e.g., rheumatoid arthritis and osteoarthritis), asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, inflammation (e.g., liver inflammation, renal inflammation, and the like), burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, urticaria, systemic lupus erythematosus, AIDS, AIDS dementia, chronic neurodegenerative disease, pain (e.g., chronic pain and post-surgical pain), priapism, cystic fibrosis, amyotrophic lateral sclerosis, schizophrenia, depression, premenstrual syndrome, anxiety, addiction, headache, migraine, Huntington's disease, epilepsy, neurodegenerative disorders, gastrointestinal motility disorders, obesity, hyperphagia, solid tumors (e.g., neuroblastoma), malaria, hematologic cancers, myelofibrosis, lung injury, graftversushost disease, head injury, CNS trauma, hepatitis, renal failure, liver disease (e.g., chronic hepatitis C), drug-induced lung injury (e.g., paraquat), myasthenia gravis (MG), ophthalmic diseases, postangioplasty, restenosis, angina, coronary artery disease, and the like.

In accordance with another embodiment of the present invention, there are provided methods for the preparation of modified NSAIDs, said method comprising covalently attaching a NSAID to a sulfur-containing functional group containing an optionally substituted hydrocarbyl moiety. The resulting compound provides a latent form of the pharmacologically active agent, releasing the biological activity thereof only when the compound is cleaved (e.g., by an esterase, amidase or other suitable enzyme).

As readily recognized by those of skill in the art, invention compounds can be prepared in a variety of ways. See, for example, Schemes 1A and 1B, wherein NSAID, X, bearing a carboxylic moiety can be reacted either directly with the sulfur-containing functional group (Scheme 1A) or indirectly through a linker molecule (Scheme 1B).

Scheme 1A

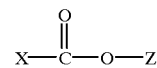

Scheme 1B

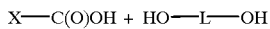

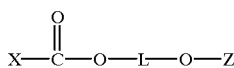

Employing these general reaction schemes, invention modified NSAIDs can be prepared from a wide variety of pharmacologically active agents. See, for example, Examples 1–59 provided herein.

In accordance with yet another embodiment of the present invention, there are provided methods for reducing the side effects induced by administration of NSAIDs to a subject, said method comprising reducing the $C_{max}$ relative to unmodified NSAIDs while maintaining a therapeutically effective concentration in plasma upon administration to a subject in need thereof. The reduction in $C_{max}$ is achieved, for example, by covalently attaching a sulfur-containing functional group containing an optionally substituted hydrocarbyl moiety to said NSAID prior to administration to said subject, as depicted in Schemes 1A and 1B.

In a particular embodiment of the invention, the $C_{max}$ is reduced relative to the unmodified NSAID by about 10% to 90%. In a presently preferred embodiment, the $C_{max}$ is reduced relative to the unmodified NSAID by about 20% to 80%. In a most preferred embodiment, the $C_{max}$ is reduced relative to the unmodified NSAID by about 40% to 70%.

In accordance with still another embodiment of the present invention, there are provided methods for enhancing the effectiveness of NSAIDs, said method comprising reducing the $C_{max}$ relative to unmodified NSAIDs while maintaining a therapeutically effective concentration in plasma upon administration to a subject in need thereof. The enhanced effectiveness of said NSAIDs is achieved, for example, by covalently attaching a sulfur-containing functional group containing an optionally substituted hydrocarbyl moiety to said NSAID.

In accordance with a still further embodiment of the present invention, there are provided improved methods for the administration of NSAIDs to a subject for the treatment of a pathological condition, the improvement comprising reducing the $C_{max}$ relative to unmodified NSAIDs while maintaining a therapeutically effective concentration in plasma upon administration to a subject in need thereof. The improvement is accomplished, for example, by covalently attaching said NSAID to a sulfur-containing functional group containing an optionally substituted hydrocarbyl moiety prior to administration thereof to said subject.

Those of skill in the art recognize that the modified NSAIDs described herein can be delivered in a variety of ways, such as, for example, orally, intravenously, subcutaneously, parenterally, rectally, by inhalation, and the like.

Depending on the mode of delivery employed, the modified NSAIDs contemplated for use herein can be delivered in a variety of pharmaceutically acceptable forms. For example, the invention modified NSAIDs can be delivered in the form of a solid, solution, emulsion, dispersion, micelle, liposome, and the like.

Thus, in accordance with still another embodiment of the present invention, there are provided physiologically active composition(s) comprising invention modified NSAIDs in a suitable vehicle rendering said compounds amenable to oral delivery, transdermal delivery, intravenous delivery, intramuscular delivery, topical delivery, nasal delivery, and the like.

Pharmaceutical compositions of the present invention can be used in the form of a solid, a solution, an emulsion, a dispersion, a micelle, a liposome, and the like, wherein the resulting composition contains one or more of the modified NSAIDs of the present invention, as an active ingredient, in admixture with an organic or inorganic carrier or excipient suitable for enteral or parenteral applications. Invention modified NSAIDs may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention modified NSAIDs are included in the pharmaceutical composition in an amount sufficient to produce the desired effect upon the process or disease condition.

Pharmaceutical compositions containing invention modified NSAIDs may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention modified NSAIDs in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the invention modified NSAIDs are mixed with an inert solid diluent, for example, calcium carbonate, calcium phosphate or kaolin. They may also be in the form of soft gelatin capsules wherein the invention modified NSAIDs are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention modified NSAIDs contemplated for use in the practice of the present invention may also be administered in the form of suppositories for rectal administration of the drug. These compositions may be prepared by mixing the invention modified NSAIDs with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

In general, the dosage of invention modified NSAIDs employed as described herein falls in the range of about 0.01 mmoles/kg body weight of the subject/hour up to about 0.5 mmoles/kg/hr. Typical daily doses, in general, lie within the range of from about 10 μg up to about 100 mg per kg body weight, and, preferably within the range of from 50 μg to 10 mg per kg body weight and can be administered up to four times daily. The daily IV dose lies within the range of from about 1 μg to about 100 mg per kg body weight, and, preferably, within the range of from 10 μg to 10 mg per kg body weight.

In accordance with yet another embodiment of the present invention, there are provided improved methods for the treatment of a subject suffering from a pathological condition by administration thereto of a NSAID, the improvement comprising reducing the $C_{max}$ relative to unmodified NSAIDs while maintaining a therapeutically effective concentration in plasma upon administration to a subject in need thereof. The improvement is achieved, for example, by covalently attaching said NSAID to a sulfur-containing functional group containing an optionally substituted hydrocarbyl moiety prior to administration thereof to said subject.

Thus, invention method for the treatment of a subject afflicted with a pathological condition comprises administering to a subject an effective amount of a modified pharmacologically active agent, wherein said pharmacologically active agent is a NSAID, and is effective for treatment of said condition, and wherein said pharmacologically active agent has been modified to reduce the $C_{max}$ relative to unmodified NSAIDs while maintaining a therapeutically effective concentration in plasma upon administration to a subject in need thereof. The modification is accomplished, for example, by the covalent attachment to the NSAID of a sulfur-containing functional group containing an optionally substituted hydrocarbyl moiety.

The invention will now be described in greater detail by reference to the following non-limiting examples.

The syntheses described in Examples 1–8 are outlined in Scheme 2.

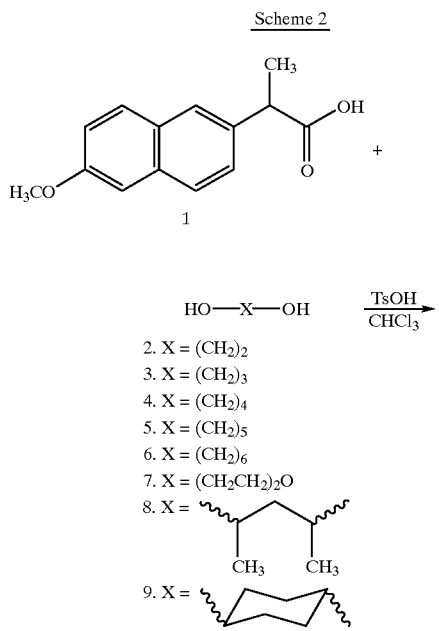

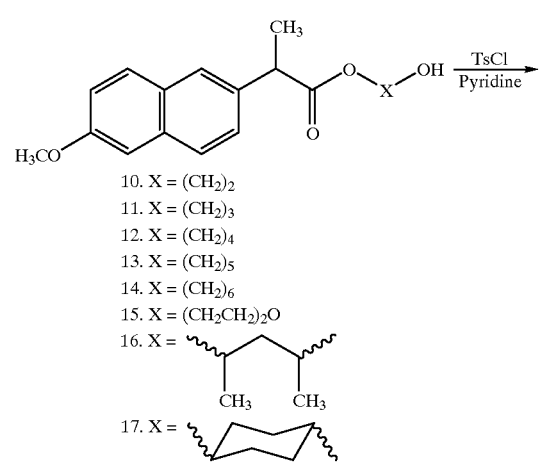

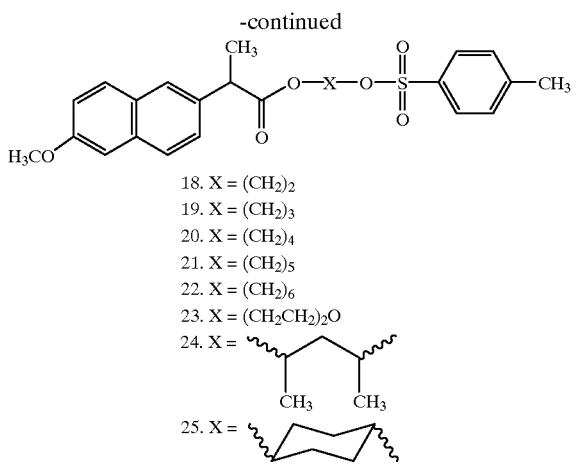

18. X = (CH₂)₂
19. X = (CH₂)₃
20. X = (CH₂)₄
21. X = (CH₂)₅
22. X = (CH₂)₆
23. X = (CH₂CH₂)₂O
24. X = [branched structure with two CH₃ groups]
25. X = [cyclohexyl structure]

EXAMPLE 1

Compound 10 (Scheme 2). A mixture of Naproxen (1) (23 g, 0.1 mol), ethylene glycol (2) (27.9 ml, 0.5 mol) and toluenesulfonic acid (TsOH) (1.27 g, 6.7 mmol) in CHCl₃ was heated to reflux for 4 h. The reaction solution was washed with water, 10% Na₂CO₃ solution and water. The organic layer was dried (Na₂SO₄) and the solvent was evaporated. The residue was purified by crystallization from CH₂Cl₂ and hexanes to give 25.7g (94%) of the compound 10 as a white crystal; $^1$H NMR (CDCl₃) δ1.59 (d, 3H), 1.62 (br, 1H, ex D₂O), 3.74 (t, 2H), 3.90 (q, 1H), 3.91 (s, 3H), 4.21 (t, 2H), 7.39 (d, 1H), 7.69 (m, 3H); $^{13}$C NMR (CDCl₃) δ18.7, 45.6, 55.5, 61.4, 66.6, 105.8, 119.3, 126.1, 126.2, 127.5, 129.1, 129.5, 133.9, 135.7, 157.9, 175.2; MS (ESI) m/z 273 (M−1).

Compound 18 (Scheme 2). To a solution of compound 10 (24.5 g, 89 mmol) in 100 ml of pyridine was added tosyl chloride (TsCl) (34.1 g, 179 mmol). The resulting solution was stirred at 0° C. for 2.5 h. The reaction solution was then poured into 300 ml of water and then 200 ml of ether was added. The layers were separated and the organic phase was washed with water (300×5) and dried (NaSO₄). After the solvent was evaporated, the residue was purified by column chromatography on a silica gel column using dichloromethane as an eluent to give 35.1 g (92%) of the pale yellow oil; $^1$H NMR (CDCl₃) δ1.55(d, 3H), 2.40 (s, 3H), 3.91 (q, 1H), 4.18 (m, 4H), 7.12 (m, 2H), 7.24 (m, 2H), 7.37 (d, 1H), 7.66 (d, 1H), 7.70 (m, 4H); MS (ESI) m/z 429 (M+1).

EXAMPLE 2

Compound 11 (Scheme 2). Compound 11 was prepared as described above for the preparation of compound 10, this time employing naproxen (1) and 1,3-propanediol (3). The resulting compound 11 was purified by crystallization from dichloromethane and hexanes with a 92% yield. $^1$H NMR (CDCl₃) δ 1.59 (d, 3H), 1.78 (m, 2H), 1.87 (br, 1H, D₂O ex), 3.53 (t, 2H), 3.87 (q, 1H), 3.91 (s, 3H), 4.23 (t, 2H), 7.11 (d, 1H), 7.15 (m, 1H), 7.41 (q, 1H), 7.66 (d, 1H), 7.69 (s, 1H), 7.71 (s, 1H); $^{13}$C NMR (CDCl₃) δ18.6, 31.8 45.7, 55.5, 59.2, 61.9, 77.0, 77.2, 77.5, 105.8, 119.2, 126.1, 126.3, 127.4, 129.1, 129.4, 133.9,135.7,157.8, 175.3; and MS (ESI) m/z 289.4 (M+1).

Compound 19 (Scheme 2). Compound 19 was prepared as described above for the preparation of compound 18, this time employing compound 11 and TsCl. Compound 19 was purified by crystallization from ether and hexane with an yield of 95%; $^1$H NMR (CDCl₃) δ1.54 (d, 3H), 1.91 (m, 2H), 2.42 (s, 3H), 3.79 (q, 1H), 3.92 (s, 3H), 3.99 (t, 2H), 4.10 (t, 2H), 7.11 d, 1H), 7.15 (q, 1H), 7.26 (d, 2H), 7.34 (d, 2H), 7.62(d, 1H,), 7.70 (m, 4H); $^{13}$C NMR (CDCl₃) δ18.5, 21.8, 28.4, 45.5, 55.5, 60.6, 66.9, 105.8, 119.2, 126.0, 126.3, 127.4, 128.0, 129.1, 129.5, 130.1, 133.1, 133.9, 135.6, 145.0, 157.9, 174.5; MS (ESI) m/z 421.1 (M−1).

EXAMPLE 3

Compound 12 (Scheme 2). Compound 12 was prepared as described above for the preparation of compound 10, this time employing naproxen (1) and 1,4-butanediol (4). Compound 12 was purified by crystallization from dichloromethane and hexanes with a 90% yield; $^1$H NMR (CDCl₃) δ1.48 (m, 2H), 1.59 (d, 3H), 1.64 (m, 2H), 1.85 (s, 1H, D₂O, ex), 3.52 (t, 2H), 3.85 (q, 1H), 3.89 (s, 3H), 4.10 (t, 2H), 7.10–7.15 (m, 2H), 7.42 (d, 1H), 7.66–7.7- (m, 3H); MS (ESI) m/z 325.4 (M+Na).

Compound 20 (Scheme 2). Compound 20 was prepared as described above for the preparation of compound 18, this time employing compound 12 and TsCl. The compound 20 was purified by crystallization from ether and hexane with an yield of 93%; $^1$H NMR (CDCl₃) δ1.55 (d, 3H), 1.53–1.62 (m, 4H), 2.43 (s, 3H), 3.82 (q, 1H), 3.92 (s, 3H), 3.94 (m, 2H), 4.02 (m, 2H), 7.11–7.15 (m, 2H), 7.30 (d, 2h), 7.38 (d, 1H), 7.64 (d, 1H), 7.70 (d, 2H), 7.75 (d, 2H); MS (ESI) m/z 457.5 (M+1).

EXAMPLE 4

Compound 13 (Scheme 2). Compound 13 was prepared as described above for the preparation of compound 10, this time employing naproxen (1) and 1,5-pentanediol (5). After reaction, the reaction solution was washed with water and the reaction solvent was then evaporated under high vacuum to give a quantitative yield of the compound 13. The compound was used to make compound 21 without further purification; $^1$H NMR (CDCl₃) δ1.28 (m, 2H), 1.46 (m, 2H), 1.55 (d, 3H), 1.59 (m, 2H), 3.51 (t, 2H), 3.85 (q, 1H), 3.91 (s, 3H), 4.09 (t, 2H), 7.11–7.15 (m, 2H), 7.40 (q, 1H), 7.66–7.70 (m, 3H); MS (ESI) m/z 317.5 (M+1).

Compound 21 (Scheme 2). Compound 21 was prepared as described above for the preparation of compound 18, this time employing compound 13 and TsCl. Compound 21 was purified by crystallization from ether and hexane with a 95% yield; $^1$H NMR (CDCl₃) δ1.24 (m, 2H), 1.48–1.58 (m, 4H), 1.59 (d, 3H), 2.43 (s, 3H), 3.84 (q, 1H), 3.89 (t, 2H), 3.91 (s, 3H), 4.01 (t, 2H),7.11–7.15 (m, 2H), 7.32 (q, 2H), 7.39 (q, 1H), 7.65 (d, 1H), 7.70 (m, 2H), 7.75 (d, 2H); MS (ESI) m/z 471.7 (M+1).

EXAMPLE 5

Compound 14 (Scheme 2). Compound 14 was prepared as described above for the preparation of compound 10, this time employing naproxen (1) and 1,6-hexanediol (6). After reaction, the reaction solution was washed with water and the reaction solvent was then evaporated to give compound 14 as a solid. The compound was used to make compound 22 without further purification; $^1$H NMR (CDCl₃) δ1.24 (m, 4H), 1.43 (m 2H), 1.56 (d, 3H), 1.54 (m, 2H), 3.51 (t, 2H), 3.85 (q, 1H), 4.01 (m, 2H), 7.10–7.15 (m 2H), 7.40 (q, 1H), 7.66–7.70 (m, 3H); MS (ESI) m/z 331.7 (M+1).

Compound 22 (Scheme 2). Compound 22 was prepared as described above for the preparation of compound 18, this time employing compound 14 and TsCl. Compound 22 was purified by column chromatography on a silica gel column using dichloromethane as an eluent to give compound 22 as a pale yellow oil; $^1$H NMR (CDCl$_3$) δ1.12–1.22 (m, 4H), 1.46–1.52 (m, 4H), 1.57 (d, 3H), 2.43 (s, 3H), 3.84 (q, 1H), 3.92 (s, 3H), 3.93 (m, 2H), 4.03 (m, 2H), 7.11–7.77 (m, 10H); MS (ESI) m/z 485.6 (M+1).

EXAMPLE 6

Compound 15 (Scheme 2). Compound 15 was prepared as described above for the preparation of compound 10, this time employing naproxen (1) and di(ethylene glycol) (7). After reaction, the reaction solution was washed with water and the reaction solvent was then evaporated to give compound 15. The compound was used to make compound 23 without further purification; $^1$H NMR (CDCl$_3$) δ1.58 (d, 3H), 1.93 (br, 1H, D$_2$O ex), 3.43 (t, 2H), 3.59 (t, 2H), 3.62 (t, 2H), 3.89 (q, 1H), 3.90 (s, 3H), 4.25 (m, 2H), 7.11–7.15 (m, 2H), 7.40–7.42 (m, 1H), 7.70 (t, 3H); $^{13}$C NMR (CDCl$_3$) δ18.7, 45.6, 55.5 61.8, 64.0, 69.2, 72.4, 76.9, 77.2, 77.5, 105,7, 119.2, 126.2, 126.4, 127.3, 129.0, 133.9, 135.7, 157.9, 174.8; MS(ESI) m/z 319.3 (M+1).

Compound 23 (Scheme 2). Compound 23 was prepared as described above for the preparation of compound 18, this time employing compound 15 and TsCl. Compound 23 was purified by column chromatography on a silica gel column using dichloromethane as an eluent to give the compound as a pale yellow oil with a 93% yield. $^1$H NMR (CDCl$_3$) δ1.58 (d, 3H), 2.41 (s, 3H), 3.43 (m, 2H), 3.48(m, 2H), 3.84 (q, 1H), 3.86 (s, 3H), 3.94 (t, 2H), 4.10 (m, 2H), 7.10–7.13 (m, 2H), 7.29 (d, 2H), 7.39 (d, 1H), 7.65–7.75 (m, 5H); $^{13}$C NMR (CDCl$_3$) δ18.6, 21.8, 45.5, 55.5, 63.9, 68.7, 69.27, 69.27, 105.8, 119.2, 126.2, 126.4, 127.4, 128.1, 129.0, 129.4, 129.9, 133.9, 145.0, 157.9, 174.7; MS (ESI) m/z 473.4 (M+1).

EXAMPLE 7

Compound 16 (Scheme 2). Compound 16 was prepared as described above for the preparation of compound 10, this time employing naproxen (1) and 1,3-pentanediol (8). After reaction, the reaction solution was washed with water and the reaction solvent was then evaporated to give compound 15 with a 32% yield. The compound was used to make compound 24 without further purification; $^1$H NMR, $^{13}$C NMR and MS are consistent with the structure of compound 16.

Compound 24 (Scheme 2). Compound 24 was prepared as described above for the preparation of compound 18, this time employing compound 16 and TsCl. The compound 24 was purified by column chromatography on a silica gel column using dichloromethane as an eluent to give the compound as a pale yellow oil with a 82% yield. The $^1$H NMR, $^{13}$C NMR and MS are consistent with the structure of compound 24.

EXAMPLE 8

Compound 17 (Scheme 2). Compound 17 was prepared as described above for the preparation of compound 10, this time employing naproxen (1) and 1,4-cyclohexanediol (8). After reaction, the reaction solution was washed with water and the reaction solvent was then evaporated to give compound 17. Compound 17 was used to make compound 25 without further purification; $^1$H NMR (CDCl$_3$) δ1.30–1.45 (m, 6H), 1.56 (d, 3H), 1.80–1.98 (m, 4H), 3.66 (m, 1H), 3.82 (q, 1H), 3.91 (s, 3H), 4.75 (m, 1H), 7.11 m, 2H), 7.39 (d, 1H), 7.65–7.70 (m, 3H); $^{13}$C NMR (CDCl$_3$) δ18.7, 28.2, 28.5, 32.1 32.2, 45.9, 55.5, 68.9, 72.0, 76.9, 77.2, 77.5, 105.8, 119.1, 126.0, 126.4, 127.2, 129.1, 129.5, 133.8, 136.1, 157.8, 174.4; MS (ESI) m/z 351.4 (M+Na).

Compound 25 (Scheme 2). Compound 25 was prepared as described above for the preparation of compound 18, this time employing compound 17 and TsCl. Compound 25 was purified by column chromatography on a silica gel column using dichloromethane as an eluent to give the compound as a pale yellow oil with a 93% yield; $^1$H NMR (CDCl$_3$) δ1.50–1.84 (m, 11H), 2.43 (s, 3H), 3.80 (q, 1H), 3.92 (s, 3H), 4.51 (m, 1H), 4.78 (m, 1H), 7.10–7.15 (m 2H), 7.26–7.39 (m, 3H), 7.61–7.75 (m, 5H); MS (ESI) m/z 483.5 (M+H).

The syntheses described in Examples 9–14 are outlined in Scheme 3.

Scheme 3

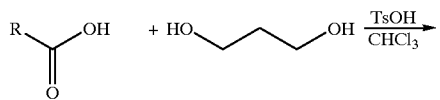

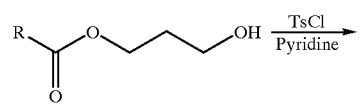

26. R = Ketoprofen
27. R = Flurbiprofen
28. R = Ibuprofen
29. R = Diclofenac
30. R = Carprofen
31. R = Indomethacin 32. R = Ketoprofen
33. R = Flurbiprofen
34. R = Ibuprofen
35. R = Diclofenac
36. R = Carprofen
37. R = Indomethacin

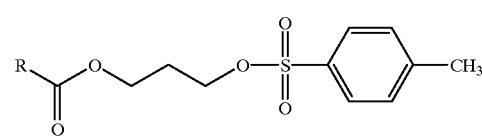

38. R = Ketoprofen
39. R = Flurbiprofen
40. R = Ibuprofen
41. R = Diclofenac
42. R = Carprofen
43. R = Indomethacin

Ketoprofen

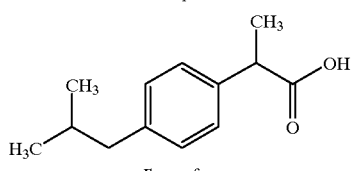

Ibuprofen

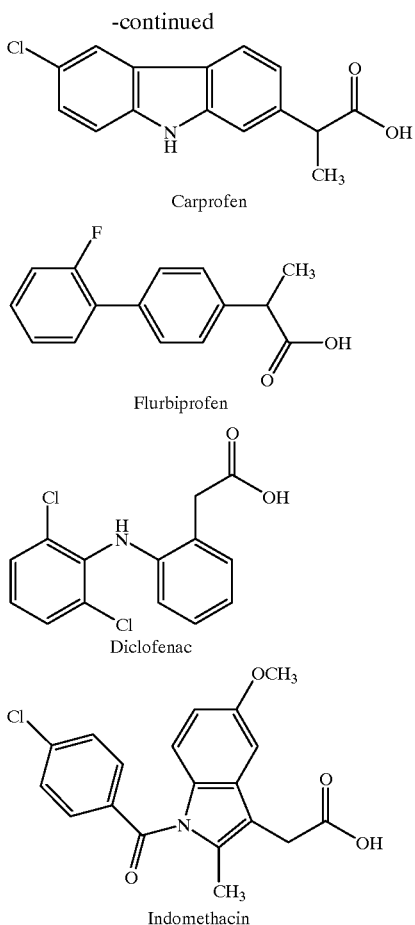

Carprofen

Flurbiprofen

Diclofenac

Indomethacin

EXAMPLE 9

Compound 32 (Scheme 3). Compound 32 was prepared as described above for the preparation of compound 10, this time employing ketoprofen (26) and 1,3-propanediol (3). Compound 32 was purified by column chromatography on a silica gel column using 200:1 $CH_2Cl_2$/MeOH as an eluent to give compound 32 with a 50% yield. $^1$H NMR (CDCl$_3$) δ1.55 (d, 3H), 1.82 (m 3H, 1H, D$_2$O ex), 3.58 (m, 2H), 3.82(m, 1H), 4.25 (m 2H), 7.44–7.82 (m, 9H); MS (ESI) m/z 313.5 (M+H).

Compound 38 (Scheme 3). Compound 38 was prepared as described above for the preparation of compound 18, this time employing compound 32 and TsCl. Compound 38 was purified by column chromatography on a silica gel column using $CH_2Cl_2$ as an eluent to give the compound 38 as a colorless oil with a 81% yield; $^1$H NMR (CDCl$_3$) δ1.49 (d, 3H), 1.94 (m, 2H), 2.43 (s, 3H), 3.72 (q, 1H), 4.01 (t, 2H), 4.12 (m, 2H), 7.31–7.78 (m, 13H); MS (ESI) m/z 467.3 (M+H).

EXAMPLE 10

Compound 33 (Scheme 3). Compound 33 was prepared as described above for the preparation of compound 10, this time employing flurbiprofen (27) and 1,3-propanediol (3). After reaction, the reaction solution was washed in water and the reaction solvent was then evaporated to give the compound 33 with a quantitative yield. The compound 33 was used to make compound 39 without further purification; $^1$H NMR (CDCl$_3$) δ1.54 (d, 3H), 1.79 (t, 1H, D$_2$O ex), 1.85 (m, 2H), 3.63 (m, 2H), 3.76 (q, 1H), 4.27 (t, 2H), 7.11–7.16 (m, 2H), 7.35–7.46 (m, 4H), 7.54 (d, 2H); MS (ESI) m/z 325.4 (M+Na).

Compound 39 (Scheme 3). Compound 39 was prepared as described above for the preparation of compound 18, this time employing compound 33 and TsCl. Compound 39 was purified by crystallization from ether/hexane system with a 79% yield; $^1$H NMR (CDCl$_3$) δ1.50 (d, 3H), 1.96 (m, 2H), 2.42 (s, 3H), 3.68 (q, 1H), 4.03 (t, 2H), 4.15 (t, 2H), 7.05–7.11 (m, 2H), 7.25–7.54 (m, 8H), 7.76 (d, 2H); $^{13}$C NMR (CDCl$_3$) δ18.4, 21.8, 28.4, 45.0, 50.8, 66.9, 115.2, 115.5, 123.68, 123.7, 127.9, 128.0, 129.2, 130.1, 131.0, 133.1, 135.6, 141.75, 141.8, 145.1, 158.9, 160.9, 173.9; MS (ESI) m/z 479.4 (M+Na).

EXAMPLE 11

Compound 34 (Scheme 3). Compound 34 was prepared as described above for the preparation of compound 10, this time employing ibuprofen (28) and 1,3-propanediol (3). After reaction, the reaction solution was washed in water and the reaction solvent was then evaporated to give compound 34 with a quantitative yield. The compound 34 was used to make compound 40 without further purification; $^1$H NMR (CDCl$_3$) δ0.89 (d, 6H), 1.49 (d, 3H), 1.79 (t, 2H), 1.78–1.85 (m, 1H), 1.95 (t, 1H, D$_2$O ex), 2.45 (d, 2H), 3.53 (m, 2H), 3.71 (q, 1H), 4.22 (m, 2H), 7.09 (d, 2H), 7.26 (d, 2H).

Compound 40 (Scheme 3). Compound 40 was prepared as described above for the preparation of compound 18, this time employing compound 34 and TsCl. Compound 40 was purified by crystallization from ether/hexane system to give a white solid with a 96% yield; $^{13}$H NMR (CDCl$_3$) δ0.89 (d, 6H), 1.44 (d, 3H), 1.81–1.92 (m, 3H), 2.44 (s, 3H), 3.61 (q, 1H), 3.99 (t, 2H), 4.09 (t, 2H), 7.08 (d, 2H), 7.14 (d, 2H), 7.34 (d, 2H), 7.78 (d, 2H); $^{13}$C NMR (CDCl$_3$) δ18.46, 21.80, 22.54, 28.39, 30.32, 45.16, 60.39, 66.92, 127.23, 128.04, 129.50, 130.03, 133.12, 137.68, 140.76, 145.00, 174.54; MS (ESI) m/z 441.5 (M+Na).

EXAMPLE 12

Compound 35 (Scheme 3). Compound 35 was prepared as described above for the preparation of compound 10, this time employing diclofenac (29) and 1,3-propanediol (3). After reaction, compound 35 was purified by column chromatography on a silica gel column using 200:1 $CH_2Cl_2$/MeOH as an eluent to give the compound 35 as a white solid with a 56% yield. $^1$H NMR (CDCl$_3$) δ1.89 (m, 3H, 1H D$_2$O ex), 3.66 (t, 2H), 3.83 (s, 3H), 4.31 (t, 2H), 6.55 (d, 1H), 6.87 (br, 1H), 6.94–7.00 (m, 2H), 7.11–7.14 (m, 1H), 7.22–7.26 (m, 1H), 7.34 (d, 2H); MS (ESI) m/z 376.3 (M+Na).

Compound 41 (Scheme 3). Compound 41 was prepared as described above for the preparation of compound 18, this time employing compound 35 and TsCl. Compound 41 was purified by column chromatography on a silica gel column using $CH_2Cl_2$ as an eluent to give the compound 41 as a pale yellow oil and the yield was 89%; ; H NMR (CDCl$_3$) δ2.02 (m, 2m,), 2.43 (s, 3H), 3.73 (s, 2H), 4.09 (t, 21), 4.17 (t, 2H), 6.53 (d, 1H), 6.99 (s, 1H), 6.93–7.00 (m, 21), 7 .12 (t, 1H), 7.18 (d, 1H), 7.23 (d, 11), 7.31–7.35 (m, 3H), 7.78 (d, 21H); MS (ESI) m/z 508.3 (M).

EXAMPLE 13

Compound 36 (Scheme 3). Compound 36 was prepared as described above for the preparation of compound 10, this time employing carprofen (30) and 1 ,3-propanediol (3).

After reaction, compound 36 was purified by column chromatography on a silica gel column using 200:1 $CH_2Cl_2$/MeOH as an eluent to give the compound 36 as a colorless oil with a 54% yield. $^1$H NMR ($CDCl_3$) δ1.59 (d, 3H), 1.74 (br, 1H, $D_2O$ ex), 1.80 (m, 2H), 3.53–3.56 (m, 2H), 3.88 (q, 1H), 4.22–4.28 (m, 2H), 7.17 (d, 1H), 7.29–7.35 (m, 3H), 7.94–7.98 (m, 2H), 8.14 (br, 1H); $^{13}$C NMR ($CDCl_3$) δ18.99, 31.84, 46.17, 59.42, 62.10, 109.70, 111.79, 119.79, 120.21, 120.87, 121.92, 124.49, 125.22, 126.09, 138.24, 139.37, 140.55, 175.39; MS (ESI) m/z 332.2 (M+H).

Compound 42 (Scheme 3). Compound 42 was prepared as described above for the preparation of compound 18, this time employing compound 36 and TsCl. Compound 42 was purified by column chromatography on a silica gel column using $CH_2Cl_2$ as an eluent to give the compound 42 as a sticky oil and the yield was 90%; $^1$H NMR ($CDCl_3$) δ1.55 (d, 3H), 1.91 (m, 2H), 2.39 (s, 3H), 3.83 (q, 1H), 3.97 (t, 2H), 4.09–4.18 (m, 2H), 7.10 (d, 2H), 7.21(d, 2H), 7.32 (s, 2H), 7.38 (s, 1H)7.65 (d, 2H), 7.91 (d, 1H), 7.98 (s, 1H), 8.54 (s, 1H); $^{13}$C NMR ($CDCl_3$) δ18.83, 21.77, 28.32, 46.08, 60.59, 57.04, 109.97, 111.97, 119.58, 120.06, 120.69, 121.77, 124.38, 125.00, 125.99, 127.95, 129.22, 130.06, 132.90, 138.38, 139.19,140.69, 145.15,174.59; MS (ESI) m/z 486.3 (M+H).

EXAMPLE 14

Compound 37 (Scheme 3). Compound 37 was prepared as described above for the preparation of compound 10, this time employing indomethacin (31) and 1,3-propanediol (3). After reaction, compound 37 was purified by column chromatography on a silica gel column using 200:1; 100:1 $CH_2Cl_2$/MeOH as an eluents to give the compound 37 as a pale yellow oil with a 49% yield. $^1$H NMR, $^{13}$C NMR and MS are consistent with the structure of compound 37.

Compound 43 (Scheme 3). Compound 43 was prepared as described above for the preparation of compound 18, this time employing compound 37 and TsCl. The compound 43 was purified by column chromatography on a silica gel column using hexane:ethyl acetate (3:1) as an eluent to give the compound 43 as a pale yellow oil and the yield was 71%; $^1$H NMR ($CDCl_3$) δ1.97 (m, 2H), 2.36 (s, 3H), 2.44 (s, 3H), 3.63 (s, 2H), 3.83 (s, 3H), 4.05 (t, 2H), 4.15 (t, 2H), 6.66–6.68 (m, 1H), 6.87 (d, 1H), 6.93 (d, 1H), 7.33 (d, 2H), 7.47 (d, 2H), 7.67 (d, 2H), 7.75 (d, 2H); MS (ESI) m/z 592.0 (M+Na)

The syntheses described in Examples 15 and 16 are outlined in Scheme 4.

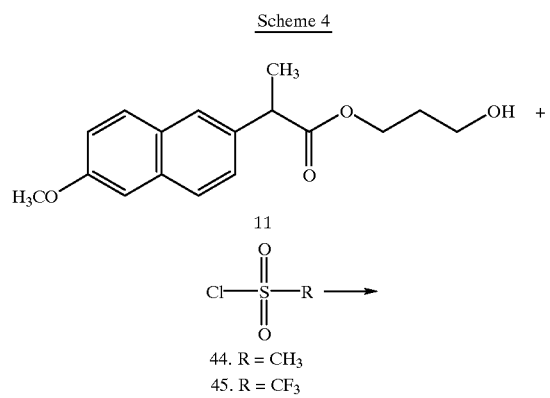

Scheme 4

44. R = CH₃
45. R = CF₃

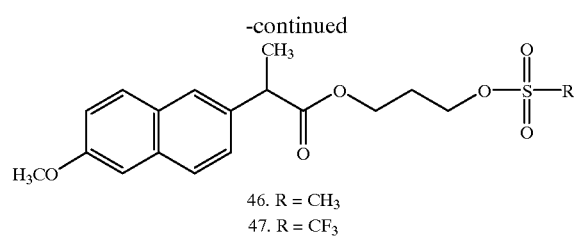

46. R = CH₃
47. R = CF₃

EXAMPLE 15

Compound 46 (Scheme 4). Compound 46 was prepared as described above for the preparation of compound 18, this time employing compound 11 and 44. The compound 46 was purified by crystallization from ether/hexane system to give the compound 46 as a white solid. The yield was 95%; $^1$H NMR ($CDCl_3$) δ1.58 (d, 3H), 2.00 (m, 2H), 2.73 (s, 3H), 3.87 (q, 1H), 3.90 (s, 3H), 4.10 (t, 2H), 4.18 (t, 2H), 7.10–7.15 (m, 2H), 7.39 (d, 1H), 7.66–7.71 (m, 3H); $^{13}$C NMR ($CDCl_3$) δ18.46,28.55, 37.03, 45.56, 55.47, 55.50, 60.38, 66.36, 105.75, 119.32, 126.09, 126.27, 127.44, 129.06, 129.41, 133.89, 135.68,157.91, 174.59; MS (ESI) m/z 388.5 (M+Na).

EXAMPLE 16

Compound 47 (Scheme 4). Compound 47 is prepared as described above for the preparation of compound 18, this time employing compound 11 and compound 45. The compound is purified by crystallization and the yield was 70–90%. The $^1$H NMR, $^{13}$C NMR and MS are consistent with the structure of compound 47.

The syntheses described in Examples 17 and 18 are outlined in Scheme 5.

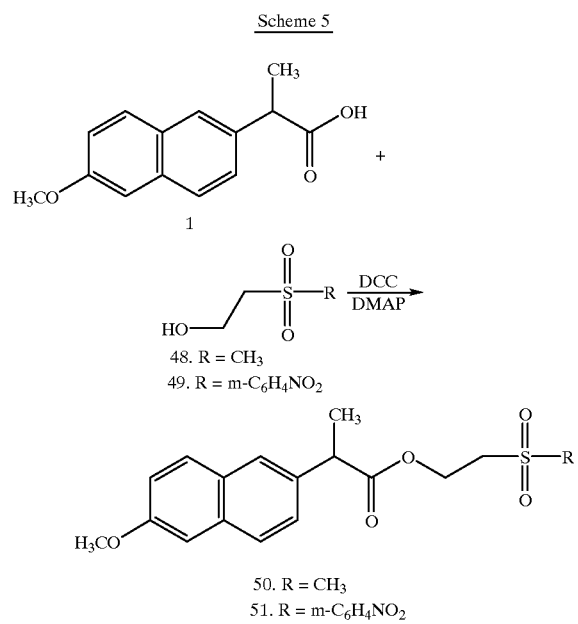

Scheme 5

48. R = CH₃
49. R = m-$C_6H_4NO_2$

50. R = CH₃
51. R = m-$C_6H_4NO_2$

EXAMPLE 17

Compound 50 (Scheme 5). To a solution of naproxen (1) (1.15 g, 5 mmol), compound 48 (0.62 g, 5 mmol) and dimethylamino pyridine (DMAP) (0.12 g, 1 mmol) was added dicyclohexyldicarbodiimide (DCC) (1.03 g, 5 mmol)

at 0° C. The resulting solution was stirred at 0° C. for 1.5 h. After reaction, the solid was filtered off and the solvent was evaporated. The residue was washed with ether to give 1.4 g (83%) of compound 50 as a white solid; $^1$H NMR (CDCl$_3$) δ1.59 (d, 3H), 2.38 (s, 3H), 3.17 (m, 2H), 3.87 (q, 1H), 3.92 (s, 3H), 4.43 (m, 1H), 4.59 (m, 1H), 7.10 (d, 1H), 7.15 (m, 1H), 7.33 (m, 1H), 7.67 (d, 1H), 7.70 (m, 2H); MS (ES) m/e 358.2 (M+Na).

EXAMPLE 18

Compound 51 (Scheme 5). Compound 51 was prepared as described above for the preparation of compound 50, this time employing compound 1 (1.15 g, 5mmol) and 49 (1.16 g, 5 mmol). The compound was purified by column chromatography on a silica gel column using 1:1 hexanes/ethyl acetate as eluent to give 0.91 g of compound 51 as a pale yellow oil; $^1$H NMR (CDCl$_3$) δ1.45 (d, 3H), 3.48 (m, 2H), 3.59 (q, 1H), 3.92 (s, 3H), 4.47 (m, 2H), 7.10 (d, 1H), 7.18 (m, 2H), 7.45 (s, 1H), 7.49 (t, 1H), 7.65 (t, 2H), 8.06 (q, 1H), 8.28 (q, 1H), 8.68 (s, 1H); $^{13}$C NMR (CDCl$_3$) δ18.8, 45.2, 55.4, 55.5, 57.9, 105,8, 123.6, 125.9, 127.5, 128.4, 129.0, 129.3, 130.8, 133.7, 133.9, 134.9, 141.5, 148.4, 158.0, 174.0.

The syntheses described in Examples 19–21 are outlined in Scheme 6.

1H), 7.32–7.35 (q, 1H), 7.62 (s, 1H), 7.67–7.71 (m, 2H); MS (ESI) m/z 358.2 (M+Na).

EXAMPLE 20

Compound 56 (Scheme 6). Compound 56 was prepared as described above for the preparation of compound 55, this time employing compound 19 and compound 53. The compound was purified by column chromatography on a silica gel column using CH$_2$Cl$_2$ as an eluent to give compound 56 as a pale yellow oil (33%). $^1$H NMR (CDCl$_3$) δ1.54 (d, 3H), 1.72 (m, 2H), 2.83 (m, 2H), 3.80 (q, 1H), 3.92 (s, 3H), 4.10 (t, 2H),7.07–8,10 (m, 10H); MS (ESI) m/z 442.3 (M+H).

EXAMPLE 21

Compound 57 (Scheme 6). Compound 57 was prepared as described above for the preparation of compound 55, this time employing compound 19 and compound 54. The compound was purified by column chromatography on a silica gel column using CH$_2$Cl$_2$ as an eluent to give compound 57 as a pale yellow oil (11%). $^1$H NMR (CDCl$_3$) δ1.55 (d, 3H), 1.80 (m, 2H), 3.03 (m 2H),3.86 (m, 1H), 4.13 (m, 2H), 7.07–7.93 (m, 10H), MS (ESI) m/z 473.4 (M+H).

The syntheses described in Examples 22 and 23 are outlined in Scheme 7.

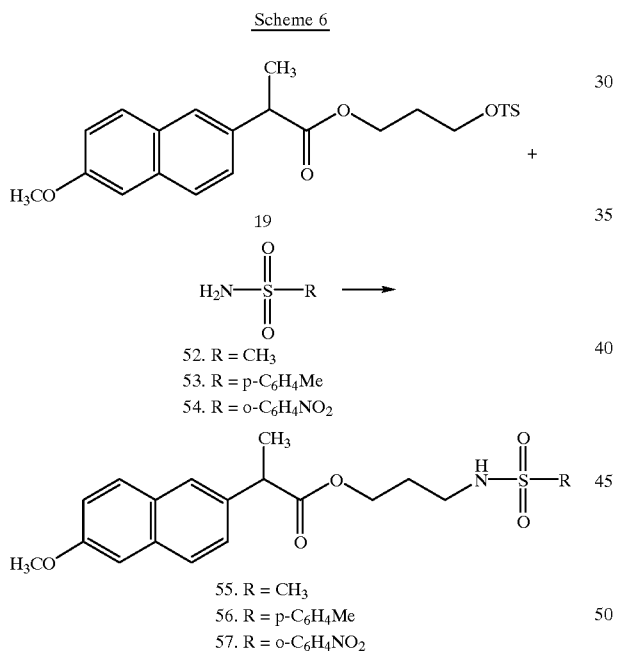

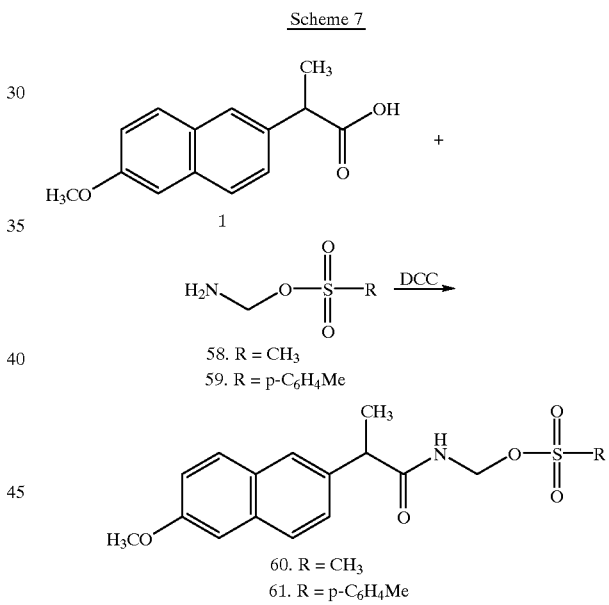

EXAMPLE 19

Compound 55 (Scheme 6). A mixture of compound 19 (2.2 g, 5 mmol), compound 52 (0.57 g, 6 mmol) and K$_2$CO$_3$ (3.45 g, 25 mmol) in 50 ml of dimethyl formamide (DMF) was stirred for a week. The reaction solution was poured into 100 ml of water and extracted with CH$_2$Cl$_2$. The organic phase was washed with water (50×5) and dried (Na$_2$SO$_4$). The solvent was evaporated and the residue was purified by column chromatography on a silica gel column using 3:1 hexane/ethyacetate as an eluent to give 0.3 g (16%) of compound 55 as a pale yellow oil; $^1$H NMR (CDCl$_3$) δ1.60 (d, 3H), 2.38 (s, 3H), 3.17 (m, 2H), 3.87 (q, 1H), 3.92 (s, 3H), 4.45 (m, 1H), 4.59 (m, 1H), 7.10 (s, 1H), 7.14–7.16 (q,

EXAMPLE 22

Compound 60 (Scheme 7). Compound 60 is prepared as described above for the preparation of compound 50, this time employing naproxen 1 and compound 58. After reaction the compound is purified by column chromatography on a silica gel column to give the compound 60 in a yield from 75–95%.

EXAMPLE 23

Compound 61 (Scheme 7). Compound 61 is prepared as described above for the preparation of compound 50, this time employing naproxen 1 and compound 59. After reaction, the compound is purified by column chromatography on a silica gel column to give compound 61 in a yield from 75–95%.

The syntheses described in Examples 24 and 25 are outlined in Scheme 8.

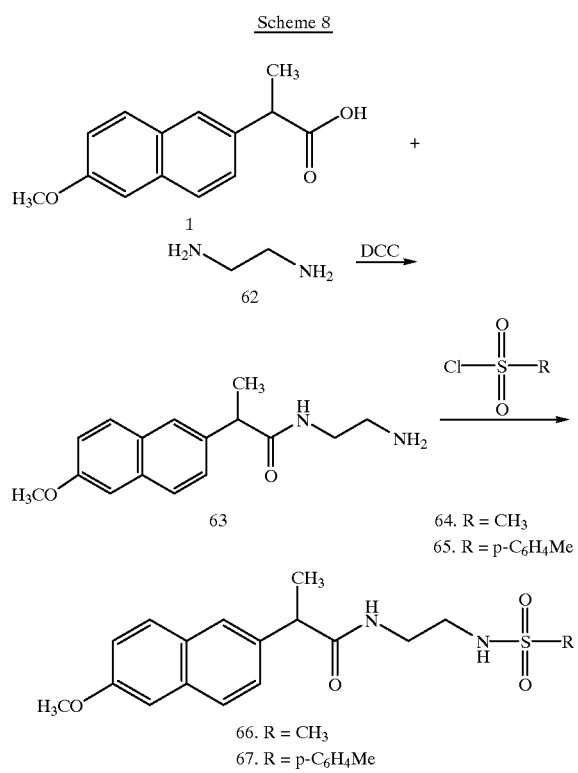

EXAMPLE 24

Compound 63 (Scheme 8). Compound 63 is prepared as described above for the preparation of compound 50, this time employing naproxen (1) and compound 62. After reaction, the compound is purified by column chromatography on a silica gel column to give compound 63 in a yield of 75–95%.

Compound 66 (Scheme 8). Compound 66 is prepared as described above for the preparation of compound 18, this time employing compound 63 and compound 64.

EXAMPLE 25

Compound 67 (Scheme 8). Compound 67 is prepared as described above for the preparation of compound 18, this time employing compound 63 and compound 65.

The syntheses described in Examples 26 and 27 are outlined in Scheme 9.

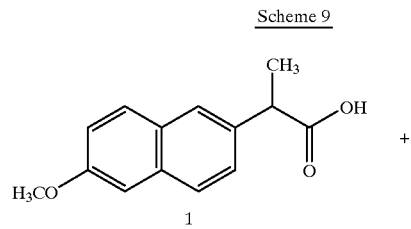

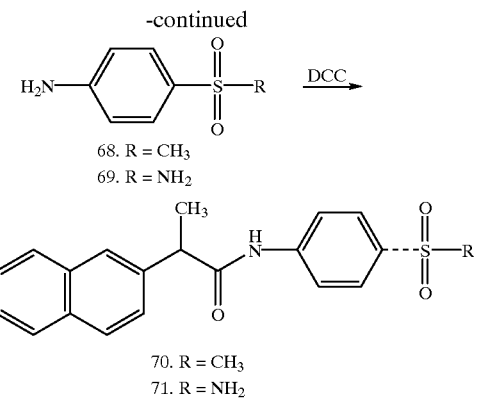

EXAMPLE 26

Compound 70 (Scheme 9). Compound 70 is prepared as described above for the preparation of compound 60, this time employing compound 1 and compound 68.

EXAMPLE 27

Compound 71 (Scheme 9). Compound 71 is prepared as described above for the preparation of compound 60, this time employing compound 1 and compound 69.

The synthesis described in Example 28 is outlined in Scheme 10.

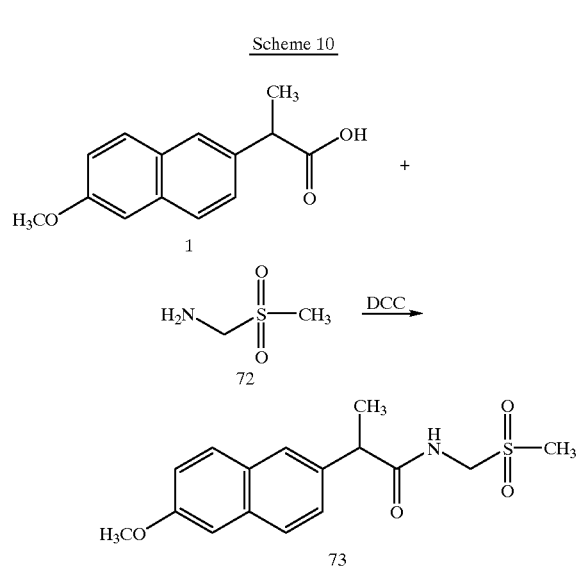

EXAMPLE 28

Compound 73 (Scheme 10). Compound 73 is prepared as described above for the preparation of compound 60, this time employing compound 1 and compound 72.

The synthesis described in Example 29 is outlined in Scheme 11.

Scheme 11

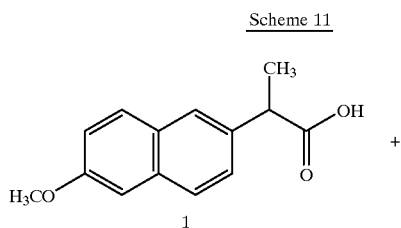

EXAMPLE 29

Compound 75 (Scheme 11). To a solution of naproxen 1 (1.15 g, 5.0 mmol) and 1,3-dicyclohexylcarbodiimide (DCC) (1.03 g, 5mmol) in 180 ml of anhydrous tedrahydrofuran (THF) was added 4-(2-aminoethyl)benzenesulfonamide 74 (1.1 g, 5.5 mmol) at rt. The resulting mixture was stirred overnight. The resulted solid was filtered off and the solvent was evaporated. The residue was partially dissolved in ethyl acetate and filtered to remove more solid. The filtrate was evaporated and the residue was purified by flash chromatography on a silica gel column using $CH_2Cl_2$ and 100:1 $CH_2Cl_2$-MeOH as eluents to give 0.1 g (5%) of the compound 75 as a white solid; $^1$H NMR (DMSO-$d_6$) δ1.38 (d, 3H), 2.73 (m, 3H, 1H, ex $D_2O$), 3.68 (q, 1H), 3.86 (s, 3H), 7.13–8.08 (m, 12H, 2H, ex $D_2O$); MS (ESI) m/z 413.1 (M +H)$^+$($C_{22}H_{25}N_2O_4S$ requires 413.5).

The syntheses described in Examples 30 and 31 are outlined in Scheme 12.

Scheme 12

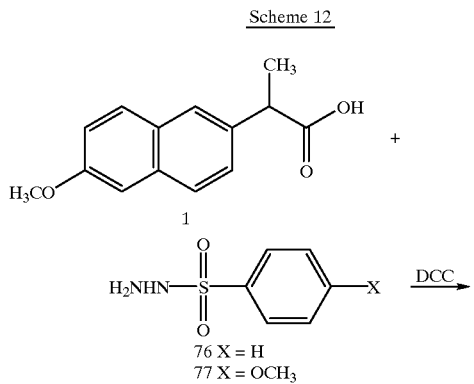

-continued

78 X = H
79 X = OCH$_3$

EXAMPLE 30

Compound 78 (Scheme 12). To a solution of naproxen 1 (1.15 g, 5 mmol) and benzenesulfonyl hydrazide 76 (0.86 g, 5 mmol) in 50 ml of $CH_2Cl_2$ was added DCC (1.03 g, 5 mmol) at rt. The resulting solution was stirred at rt for 26 h. The resulted solid was filtered off and the filtrate was washed with 5% $Na_2CO_3$ solution, 0.5N HCl solution and water. The organic phase was dried with anhydrous sodium sulfate ($Na_2SO_4$) and concentrated. The residue was purified by flash chromatography on a silica gel column using 5:1 and 2:1 hexanes-EtOAc as eluents to give 1.44 g (75%) of the compound 78 as a white solid; $^1$H NMR (CDCl$_3$) δ1.37 (d, 3H), 3.54 (q, 1H), 3.94 (s, 3H), 7.12–7.77 (m, 13H, 2H, ex $D_2O$); MS (ESI) m/z 385.0 (M+H)$^+$ ($C_{20}H_{21}N_2O_4S$ requires 385.1).

EXAMPLE 31

Compound 79 (Scheme 12). Compound 79 was prepared by the similar procedure as described above for compound 78 from 4-methoxybenzenesulfonyl hydrazide 77 (1.01 g, 5 mmol), naproxen 1 (1.15 g, 5 mmol) and DCC (1.03 g, 5 mmol). The compound was purified by flash chromatography on a silica gel column using 200:1 $CH_2Cl_2$-MeOH as an eluent to give 0.69 g (33%) of the compound 79 as a white solid; $^1$H NMR (CDCl$_3$) δ1.38 (d, 3H), 3.57 (q, 1H), 3.68 (s, 3H), 3.92 (s, 3H), 6.60–8.13 (12H, 2H ex $D_2O$); MS (ESI) m/z 415.7 (M+H)$^+$ ($C_{21}H_{23}N_2O_5S$ requires 415.2).

The syntheses described in Examples 32–35 are outlined in Scheme 13.

Scheme 13

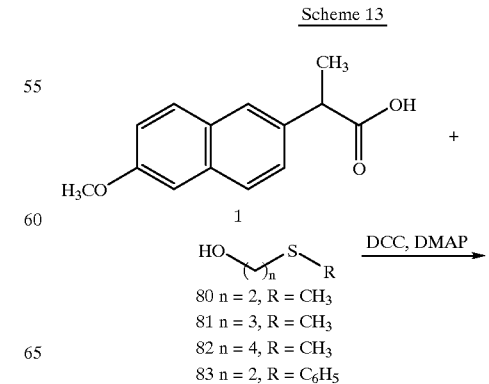

80 n = 2, R = CH$_3$
81 n = 3, R = CH$_3$
82 n = 4, R = CH$_3$
83 n = 2, R = C$_6$H$_5$

-continued

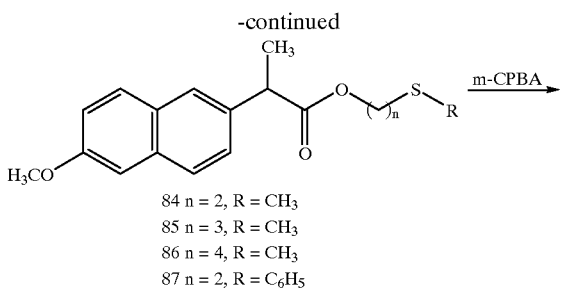

84 n = 2, R = CH₃
85 n = 3, R = CH₃
86 n = 4, R = CH₃
87 n = 2, R = C₆H₅

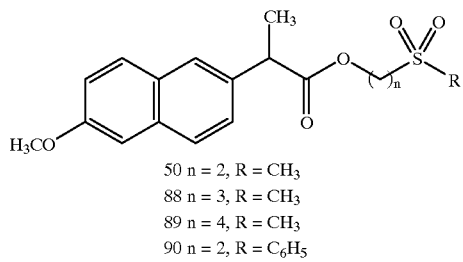

50 n = 2, R = CH₃
88 n = 3, R = CH₃
89 n = 4, R = CH₃
90 n = 2, R = C₆H₅

EXAMPLE 32

Compound 84 (Scheme 13). To a solution of naproxen 1 (1.15 g, 5 mmol) and 2-(methylthio)ethanol 80 (0.46 g, 5 mmol) and 4- (dimethylamino)pyridine (DMAP) (0.12 g, 1 mmol) in 50 ml of $CH_2Cl_2$ was added DCC (1.03 g, 5 mmol) at 0° C. The resulting solution was stirred at 0° C. for 2 h. The solid was filtered off and the solvent was evaporated. The residue was partially dissolved in EtOAc and the mixture was filtered to remove more solid. The filtrate was washed with water (50×2), dried ($Na_2SO_4$) and concentrated. Recrystallization of the crude product from hexanes provided 0.96 g of the compound 84 as a white crystal; ¹H NMR (CDCl₃) δ1.59 (d, 3H), 2.05 (s, 3H), 2.65 (m, 2H), 3.86 (q, 1H), 3.91 (s, 3H), 4.25 (m, 2H), 7.11–7.25 (m, 2H), 7.41 (d, 1H), 7.67–7.71 (m, 3H); ¹³C NMR (CDCl₃) δ15.9, 16.8, 32.6, 45.6, 55.5, 63.7, 105.8, 119.2, 126.2, 126.4, 127.4, 129.1, 129.4, 133.9, 135.7, 157.9, 174.7; MS (ESI) m/z 327.4 (M+Na)⁺ ($C_{17}H_2O_3SNa$ requires 327.1).

Compound 50 (Scheme 13). To a solution of compound 84 (0.09 g, 0.3 mmol) in 3 ml of acetone was added m-chloroperoxybenzoic acid (m-CPBA) (0.25 g, 1.5 mmol). The resulting solution was stirred at 0° C. for 3 h. A solution of $Na_2SO_3$ was added to quench the reaction and then more water was added. The resulted mixture was filtered and washed with methanol to give a compound which has the identical ¹H NMR and MS properties to compound 50 produced by the procedure set forth in Example 17 above.

EXAMPLE 33

Compound 85 (Scheme 13). Compound 85 was prepared by the similar procedure as described above for compound 84 from naproxen 1 (6.9 g, 30 mmol), methylthiopropanol 81 (3.06 ml, 3.18 g, 30 mmol), DMAP (0.72 g, 6 mmol) and DCC (6.18 g, 30 mmol). The compound was purified by recrystallization from hexanes to give 6.7 g (70%) of the compound 85 as a white crystal; ¹H NMR (CDCl₃) δ1.58 (d, 3H), 1.85 (m, 2H), 1.97 (s, 3H), 2.39 (t, 2H), 3.85 (q, 1H), 3.91 (s, 3H), 4.17 (m, 2H), 7.11–7.15 (m, 2H), 7.39–7.41 (m,1H), 7.66–7.71 (m, 3H); MS (ESI) m/z 441.5 (M+Na)⁺. ($C_{18}H_{22}O_3SNa$ requires 441.2).

Compound 88 (Scheme 13). Compound 88 was prepared by the similar procedure as described above for compound 50 from compound 85 (1.27 g, 4 mmol) and m-CPBA (3.4 g, 20 mmol). The product was purified by recrystallization from EtOAc-hexanes to give 1.1 g (80%) of the compound 88 as a white powder; ¹H NMR (CDCl₃) δ1.58 (d, 3H), 2.08 (m, 2H), 2.59 (s, 3H), 2.75 (m, 2H), 3.86 (q, 1H), 3.91 (s, 3H), 4.16 (m, 1H), 4.26 (m, 1H), 7.11–7.16 (m, 2H), 7.37–7.39 (m, 1H), 7.66 (s, 1H), 7.70–7.73 (m, 2H); MS (ESI) m/z 373.3 (M+Na)⁺ ($C_{18}H_{22}O_3SNa$ requires 373.1).

EXAMPLE 34

Compound 86 (Scheme 13). Compound 86 was prepared by the similar procedure as described above for compound 84 from naproxen 1 (6.9 g, 30 mmol), methylthiobutanol 82 (3.6 g, 30 mmol), DCC (6.18 g, 30 mmol) and DMAP (0.72 g, 6 mmol). The product was purified by recrystallization from hexanes to give 7.3 g (73%) of the compound 86 as a white solid; ¹H NMR (CDCl₃) δ1.54 (m, 2H), 1.58 (d, 3H), 1.67 (m, 2H), 1.96 (s, 3H), 2.40 (t, 2H), 3.85 (q, 1H), 3.89 (s, 3H), 4.09 (t, 2H), 7.10–7.15 (m, 2H), 7.39–7.41 (q, 1H), 7.66–7.70 (t, 3H); ¹³C NMR (CDCl₃) δ15.35, 18.59, 25.48, 27.74, 33.72, 45,61, 55.3, 64.37, 105.70, 119.08, 126.02, 126.32, 127.24, 129.04, 129.37, 133.80, 135.85,157.74, 174.76; MS (ESI) m/z 355.3 (M+Na)⁺ ($C_{19}H_{24}O_3SNa$ requires 355.1).

Compound 89 (Scheme 13). Compound 89 was prepared by the similar procedure as described above for compound 50 from compound 86 (1.33 g, 4 mmol), m-CPBA (3.5 g, 20 mmol) in 35 ml of acetone. The product was purified by recrystallization from $CH_2Cl_2$-hexane to give 1.13 g ( 78%) of the compound 89 as a pale yellow solid; ¹H NMR (CDCl₃) δ1.57 (d, 3H), 1.73 (m, 4H), 2.56 (s, 3H), 2.82 (m, 2H), 3.65 (q, 1H), 3.90 (s, 3H), 4.08 (m, 1H), 4.15 (m, 1H), 7.10–7.15 (m, 2H), 7.38–7.40 (q, 1H), 7.65 (s, 1H), 7.70 (d, 2H); ¹³C NMR (CDCl₃) δ18.5, 19.4, 27.5, 40.2, 45.6, 54.2, 55.5, 63.7, 105.8, 119.4, 126.1, 126.3, 127.4, 129.1, 129.4, 133.9, 135.8, 157.9, 174.7; MS (ESI) m/z 387.5 (M+Na)⁺ ($C_{19}H_{24}O_5SNa$ requires 3 87.5).

EXAMPLE 35

Compound 87 (Scheme 13). Compound 87 was prepared by the similar procedure as described above for compound 84 from naproxen 1 (1.15 g, 5 mmol), 2-(phenylthio)ethanol 83 (0.77 g, 5 mmol), DCC (1.03 g, 5 mmol) and DMAP (0.12 g, 1 mmol) in 50 ml of $CH_2Cl_2$. The product was purified by recrystallization from hexanes to give 1.0 g (56%) of the compound 87 as a white powder; ¹H NMR (CDCl₃) δ1.56 (d, 3H), 3.10 (m, 2H), 3.83 (q, 1H), 3.91 (s, 3H), 4.25 (m, 2H), 7.11–7.40 (m, 8H), 7.65–7.70 (m, 3H); ¹³C NMR (CDCl₃) δ18.7, 32.5, 45.6, 55.5, 63.4, 105.8, 119.2, 126.2, 126.4, 126.8, 127.4, 129.1, 129.2, 129.5, 130.1, 133.9, 135.3, 135.7, 157.9, 174.7; MS (ESI) m/z 389.5 (M+Na)⁺ ($C_{22}H_{22}O_2SNa$ requires 389.2).

Compound 90 (Scheme 13). Compound 90 was prepared by the similar procedure as described above for compound 50 from compound 87 (1.46 g, 4 mmol), m-CPBA (3.5 g, 20 mmol) in 35 ml of acetone. The product was purified by recrystallization from $CH_2Cl_2$-hexane to give 1.2 g (75%) of the compound 90 as a white solid; ¹H NMR (CDCl₃) δ1.46 (d, 3H), 3.40 (m, 2H), 3.59 (q, 1H), 3.92 (s, 3H), 4.33 (m, 1H), 4.45 (m, 1H), 7.11–7.85 (m, 11H); ¹³C NMR (CDCl₃) δ18.6, 45.2, 55.2, 55.5, 58.1, 105.8, 119.3, 126.2, 127.4, 128.3, 129.1, 129.4.129.5, 133.9, 134.1, 135.1, 139.5, 158.0, 174.2; MS (ESI) m/z 399.4 (M+H)⁺ ($C_{22}H_{23}O_5S$ requires 399.5)

The synthesis described in Example 36 is outlined in Scheme 14.

Scheme 14

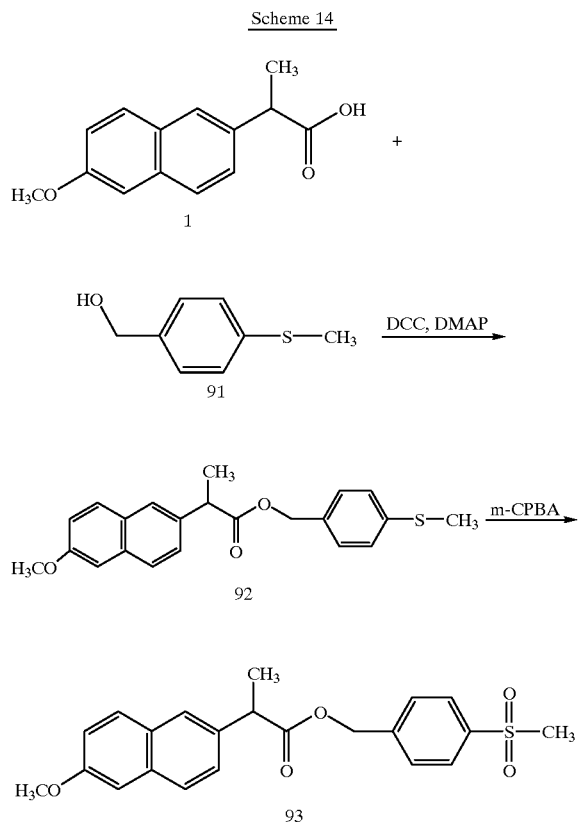

Scheme 15

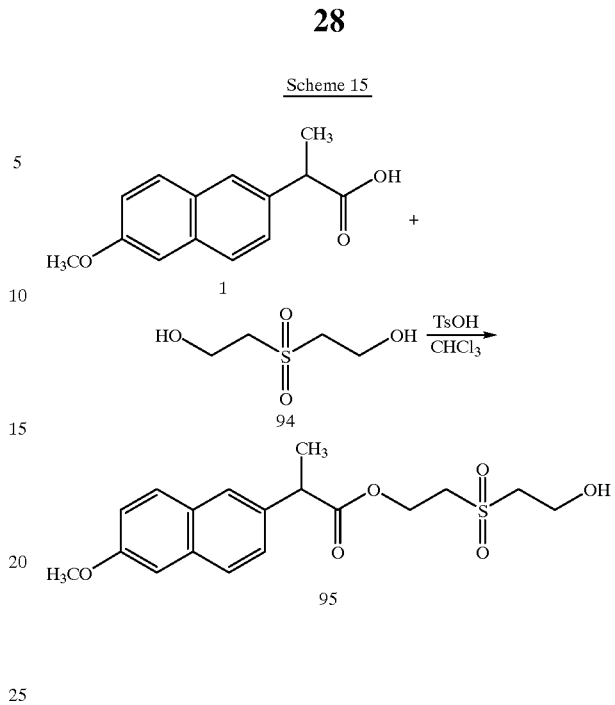

EXAMPLE 36

Compound 92 (Scheme 14). Compound 92 was prepared by the similar procedure as described above for compound 84 from methylthiobenzene alcohol 91 (4.6 g, 30 mmol), naproxen 1 (6.9 g, 30 mmol), DCC (6.18 g, 30 mmol) and DMAP (0.72 g, 6 mmol). The product was purified by recrystallization from $CH_2Cl_2$-hexanes to give 8.6 g (78%) of the compound 92 as a white crystal; $^1H$ NMR ($CDCl_3$) δ1.58 (d, 3H), 2.45 (s, 3H), 3.89 (q, 1H), 3.92 (s, 3H), 5.05 (q, 2H), 7.11–7.16 (m, 6H), 7.37–7.39 (m, 1H), 7.63–7.70 (m, 3H); $^{13}C$ NMR ($CDCl_3$) δ15.9, 18.7, 45.7, 55.5, 66.3, 105.8, 119.2, 126.2, 126.5, 126.7, 127.3, 128.9, 129.1, 129.5, 132.9, 133.9, 135.7, 138.8, 157.9, 174.6; MS (ESI) m/z 389.4 (M+Na)$^+$ ($C_{22}H_{22}O_3$Sna requires 389.5)

Compound 93 (Scheme 14). Compound 93 was prepared by the similar procedure as described above for compound 50 from compound 92 (1.1 g, 3 mmol), m-CPBA (1.34 g, 7.5 mmol) in 30 ml of acetone. The product was purified by flash chromatography on a silica gel column using $CH_2Cl_2$ as an eluent to give 1.0 g (85%) of the compound 93 as a white solid; $^1H$ NMR ($CDCl_3$) δ1.61 (d, 3H), 2.99 (s, 3H), 3.92 (s, 3H), 3.93 (q, 1H), 5.18 (q, 2H), 7.12–7.16 (m, 2H), 7.34–7.39 (m, 3H), 7.65–7.71 (m, 3H), 7.81 (d, 2H); $^{13}C$ NMR ($CDCl_3$) δ18.5, 44.7, 45.6, 55.5, 65.3, 105.8, 119.4, 126.2, 126.3, 127.5, 127.8, 128.3, 129.1, 129.4, 133.9, 135.3, 140.2, 142.5, 158.0, 174.4; MS (ESI) m/z 398.9 M$^+$ ($C_{22}H_{22}$)$_5$S requires 398.5)

The synthesis described in Example 37 is outlined in Scheme 15.

EXAMPLE 37

Compound 95 (Scheme 15). A mixture of 2,2'-sulfonyldiethanol 94 (12.5 ml, 60% in $H_2O$, 9.25 g, 60 mmol) and $CHCl_3$ was heated to reflux to remove the water and then naproxen 1 (4.6 g, 20 mmol) and 4-toluenesulfonic acid (TsOH) (0.25 g, 1.3 mmol) were added to the above mixture. The resulting mixture was continued to reflux for 6 h. The reaction mixture was washed with water twice, 10% $Na_2CO_3$ solution twice and then water once. The organic phase was dried ($Na_2SO_4$) and the solvent was evaporated. The crude product was recrystallized from $CHCl_3$-hexanes to give 0.41 g of the compound 95 as a white powder; $^1H$ NMR ($CDCl_3$) δ1.60 (d, 3H), 1.85 (bs, 1H, ex $D_2O$), 2.51–2.56 (m, 1H), 2.62–2.67 (m, 1H), 3.25–3.28 (m, 2H), 3.48–3.51 (m, 2H), 3.88 (q, 1H), 3.92 (s, 3H), 4.41–4.46 (m, 1H), 4.56–4.61 (m, 1H), 7.11 (d, 1H), 7.15–7.18 (q, 1H), 7.35–7.36 (q, 1H), 7.65 (s, 1H), 7.69–7.74 (m, 2H); $^{13}C$ NMR ($CDCl_3$) δ18.3, 45.6, 54.0, 55.5, 55.6, 56.2, 56.3, 58.6, 105.8, 119.8, 126.1, 126.4, 127.7, 129.0, 133.9, 135.2, 158.2, 173.9; MS (ESI) m/z 389.1 (M+Na)$^+$ ($C_{18}H_{22}O_6$Sna requires 389.1)

The syntheses described in Examples 38–45 are outlined in Scheme 16.

Scheme 16

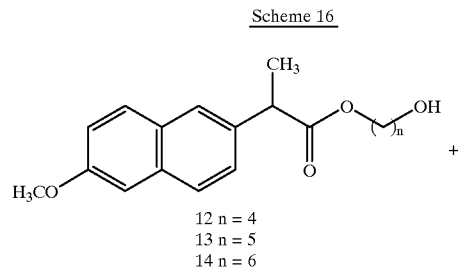

12 n = 4
13 n = 5
14 n = 6

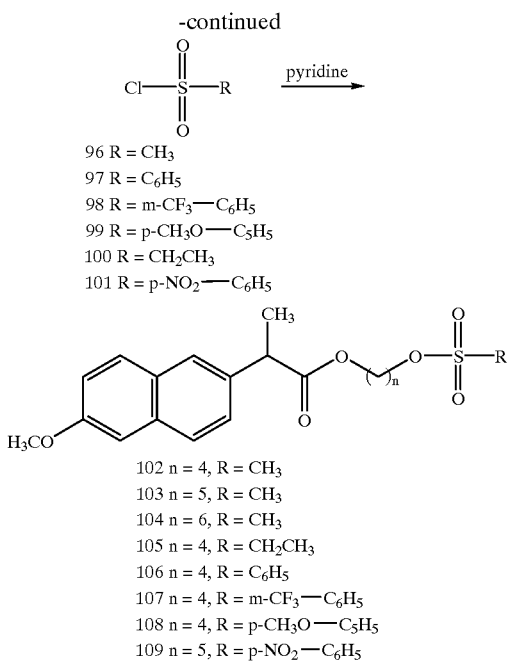

96 R = CH₃
97 R = C₆H₅
98 R = m-CF₃—C₆H₅
99 R = p-CH₃O—C₅H₅
100 R = CH₂CH₃
101 R = p-NO₂—C₆H₅

102 n = 4, R = CH₃
103 n = 5, R = CH₃
104 n = 6, R = CH₃
105 n = 4, R = CH₂CH₃
106 n = 4, R = C₆H₅
107 n = 4, R = m-CF₃—C₆H₅
108 n = 4, R = p-CH₃O—C₅H₅
109 n = 5, R = p-NO₂—C₆H₅

EXAMPLE 38

Compound 102 (Scheme 16). A solution of compound 12 (3.02 g, 10 mmol) and methanesulfonyl chloride 96 (1.55 ml, 2.29 g, 20 mmol) in 10 ml of pyridine was stirred at 0° C. for 2 h. 100 ml of water was added and the resulting mixture was filtered and the solid was washed with water five times. The compound was purified by rerecrystallization from CH₂Cl₂-hexanes to give 3.0 g (79%) of the compound 102 as a white solid; $^1$H NMR (CDCl₃) δ1.58 (d, 3H), 1.67 (m, 4H), 2.88 (s, 3H), 3.85 (q, 1H), 3.91 (s, 3H), 4.10 (m, 4H), 7.11–7.15 (m, 2H), 7.38–7.40 (q, 1H), 7.65–7.71 (s, 3H), $^{13}$C NMR (CDCl₃) δ18.6, 24.9, 25.9, 37.5, 45.6, 55.5, 63.9, 69.4, 105.8, 119.2, 126.1, 126.4, 127.4, 129.1, 129.4, 133.9, 136.8, 157.9, 174.8; MS (ESI) m/z 403.6 (M+Na)⁺ (C₁₉H₂₄O₆Sna requires 403.5).

EXAMPLE 39

Compound 103 (Scheme 16). Compound 103 was prepared by the similar procedure as described above for compound 102 from compound 13 (4.74 g, 15 mmol) and compound 96 (2.31 ml, 3.43 g, 30 mmol). The product was purified by recrystallization from CH₂Cl₂-hexanes to give 5.1 g (86%) of the compound 103 as a white solid; $^1$H NMR (CDCl₃) δ1.30 (m, 2H), 1.58 (d, 3H), 1.62(m, 4H), 2.9 (s, 3H), 3.89 (q, 1H), 3.91 (s, 3H), 4.02–4.11 (m, 4H), 7.11–7.15 (m, 2H), 7.39 (d, 1H), 7.66–7.71 (m, 3H); $^{13}$C NMR (CDCl₃) δ18.5, 22.1, 28.1, 28.8, 37.4, 45.7, 55.5, 64.5, 69.8, 105.8, 119.2, 126.1, 126.4, 127.3, 129.4, 133.9, 135.9, 157.9, 174.9; MS (ESI) m/z 395.1 (M+H)⁺ (C₂₀H₂₇O₆S requires 395.1).

EXAMPLE 40

Compound 104 (Scheme 16). Compound 104 was prepared by the similar procedure as described above for compound 102 from compound 14 (3.3 g, 10 mmol) and compound 96 (1.55 ml, 2.31 g, 20 mmol). The product was purified by recrystallization from CH₂Cl₂-hexanes to give 1.72 g (42%) of the compound 104 as a white solid; $^1$H NMR (CDCl₃) δ1.21–1.31 (m, 4H), 1.53–1.61 (m, 7H), 2.95 (s, 3H), 3.89 (q, 1H), 3.91 (s, 3H), 4.04–4.12 (m, 4H), 7.12–7.15 (m, 2H), 7.40 (q, 1H), 7.69 (t, 3H); MS (ESI) m/z 431.4 (M+Na)⁺ (C₂₁H₂₈O₆Sna requires 431.5).

EXAMPLE 41

Compound 105 (Scheme 16). Compound 105 was prepared by the similar procedure as described above for compound 103 from compound 12 (1.51 g, 5 mmol) and compound 100 (0.94 ml, 1.28 g, 10 mmol). The product was purified by flash chromatography on a silica gel column using CH₂Cl₂ as an eluent to give 1.45 g (74%) of the compound 105 as a pale yellow oil; $^1$H NMR (CDCl₃) δ1.35 (t, 3H), 1.57(d, 3H), 1.68 (m, 4H), 3.01(q, 2H), 3.84 (q, 1H), 3.90 (s, 3H), 4.11 (m, 4H); MS (ESI) m/z 417.4 (M+Na)⁺ (C₂₀H₂₆O₆Sna requires 417.5).

EXAMPLE 42

Compound 106 (Scheme 16). Compound 106 was prepared by the similar procedure as described above for compound 102 from compound 12 (1.51 g, 5 mmol) and compound 97 (1.27 ml, 1.76 g, 10 mmol). The product was washed with water and dried to give 1.9 g (86%) of the compound 106 as a pale yellow oil; $^1$H NMR (CDCl₃) δ1.53 (d, 3H), 1.55–1.63 (m, 4H), 3.81 (q, 1H), 3.91 (s, 3H), 3.94–4.03 (m, 4H), 7.11–7.15 (m, 2H), 7.36 (d, 1H), 7.51(m, 2H), 7.63 (m, 2H), 7.69 (d, 2H), 7.85 (d, 2H); MS (ESI) m/z 443.6 (M+H)⁺ (C₂₄H₂₇O₆S requires 443.5).

EXAMPLE 43

Compound 107 (Scheme 16). Compound 107 was prepared by the similar procedure as described above for compound 102 from compound 12 (1.51 g, 5 mmol) and compound 98 (1.55 ml, 2.45 g, 10 mmol). The product was purified by flash chromatography on a silica gel column using CH₂Cl₂ as an eluent to give 1.12 g (44%) of the compound 107 as a white solid; $^1$H NMR (CDCl₃) δ1.56 (d, 3H), 1.60–1.63 (m, 4H), 3.82 (q, 1H), 3.90 (s, 3H), 4.00–4.06 (m, 4H), 7.11–7.15 (m, 2H), 7.36–7.38 (q, 1H), 7.64–7.71 (m, 4H), 7.89 (d, 1H), 8.04 (d, 1H), 8.15 (s, 1H); $^{13}$C NMR (CDCl₃) δ18.5, 24.8 25.7, 45.6, 55.5, 63.7, 70.8, 105.8, 119.2, 125.06, 125.09, 126.3, 127.4, 129.1, 129.4, 130.3, 130.6, 131.2, 132.1, 133.9, 135.8, 137.6, 157.9, 174.8; MS (ESI) m/z 533.3 (M+Na)⁺ (C₂₅H₂₅F₃O₆Sna requires 533.5).

EXAMPLE 44

Compound 108 (Scheme 16). Compound 108 was prepared by the similar procedure as described above for compound 102 from compound 12 (1.51 g, 5 mmol) and compound 99 (2.06 g, 10 mmol). The product was purified by recrystallization from CH₂Cl₂-hexanes to give 1.44 g (61%) of compound 108 as a white crystal; $^1$H NMR and MS spectra are consistence with the compound 108.

EXAMPLE 45

Compound 109 (Scheme 16). Compound 109 was prepared by the similar procedure as described above for compound 102 from compound 13 (1.58 g, 5 mmol) and compound 101 (2.21 g, 10 mmol). The product was purified by flash chromatography on a silica gel column using CH₂Cl₂ as an eluent to give 1.5 g (67%) of the compound 109 as a pale yellow oil; $^1$H NMR (CDCl₃) δ1.21–1.26 (m, 2H), 1.50–1.59 (m, 7H), 3.83 (q, 1H), 3.91 (s, 3H), 3.89–4.08 (m, 4H), 7.11–7.26 (m, 2H), 7.37–7.40 (m, 1H), 7.63–7.70 (m, 3H), 8.02 (d, 2H), 8.35 (d, 2H); MS (ESI) m/z 524.6 (M+Na)⁺ (C₂₅H₂₇NO₈Sna requires 524.6).

The syntheses described in Examples 46 and 47 are outlined in Scheme 17.

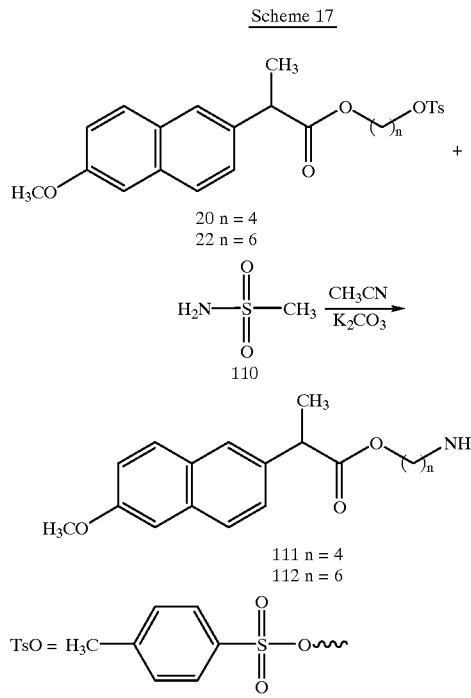

Scheme 17

EXAMPLE 46

Compound 111 (Scheme 17). A mixture of compound 20 (4.56 g, 10 mmol), methanesulfonamide 110 (1.9 g, 20 mmol, 2 equiv) and $K_2CO_3$ (6.9 g, 50 mmol, 5 equiv) in 100 ml of acetonitril ($CH_3CN$) was heated to reflux for 26 h. The solvent was evaporated and the residue was dissolved and shaken well in water and EtOAc. The two phases were separated and the organic phase was washed with water three times, dried ($Na_2SO_4$) and concentrated. The crude product was purified by recrystallization from $CH_2Cl_2$-hexanes to give 2.53 g (67%) of the compound 111 as an yellow solid; $^1H$ NMR (CDCl$_3$) δ1.38–1.42 (m, 2H), 1.53–1.63 (m, 2H), 1.58 (d, 3H), 2.77 (s, 3H), 2.92–2.96 (m, 2H), 3.85 (q, 1H), 3.91 (s, 3H), 3.99 (bs, 1H, ex D$_2$O), 4.03–4.07 (m, 1H), 4.11–4.16 (m, 1H), 7.12–7.16 (m, 2H), 7.38–7.40 (d, 1H), 7.66 (s, 1H), 7.71 (d, 2H); MS (ESI) m/z 402.5 (M+Na)$^+$ ($C_{19}H_{25}NO_5SNa$ requires 402.5).

EXAMPLE 47

Compound 112 (Scheme 17). Compound 112 was prepared by the similar procedure as described above for compound 111 from compound 22 (2.42 g, 5 mmol) and compound 110 (0.57 g, 6 mmol, 1.2 equiv). The product was purified by recrystallization from $CH_2Cl_2$-hexanes to give 0.9 g (45%) of the compound 112 as a powder; $^1H$ NMR (CDCl$_3$) δ1.17–1.22 (m, 4H), 1.33–1.37 (m, 2H), 1.56 (d, 3H), 1.52–1.60 (m, 2H), 2.89 (s, 3H), 2.95 (q, 2H), 3.85 (q, 1H), 3.91 (s, 3H), 4.01–4.15 (m, 3H, 1H ex D$_2$O), 7.12–7.15 (m, 2H), 7.40 (d, 1H), 7.66–7.76 (m, 3H); $^{13}C$ NMR (CDCl$_3$) δ18.5, 25.5, 26.1, 28.5, 30.1, 40.5, 43.2, 45.7, 55.5, 64.6, 105.8, 119.2, 126.1, 126.5, 127.3, 129.1, 129.4, 133.9, 136.1, 157.8, 174.9; MS (ESI) m/z 430.6 (M+Na)$^+$ ($C_{21}H_{29}NO_5Sna$ requires 430.6).

The syntheses described in Examples 48 and 49 are outlined in Scheme 18.

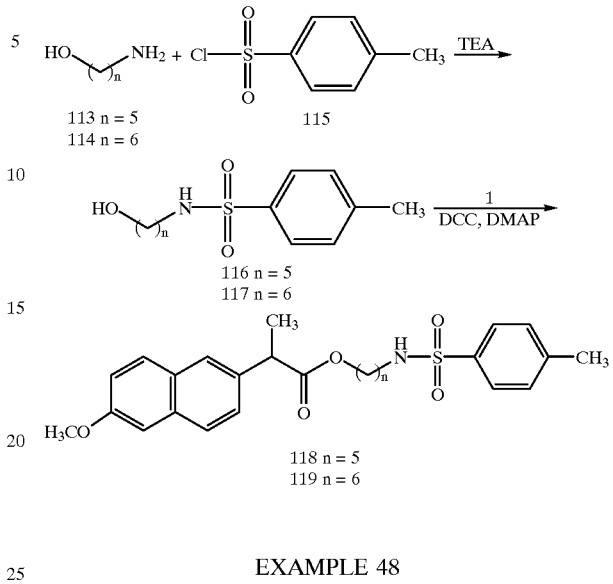

Scheme 18

EXAMPLE 48

Compound 116 (Scheme 18). To a solution of aminopentanol 113 (3.1 g, 30 mmol) and triethylamine (TEA) (4.2 ml, 3.03 g, 30 mmol) in 50 ml of anhydrous THF was added dropwise p-toluenesulfonyl chloride 115 (5.7 g, 30 mmol) in 50 ml of THF at 0° C. The resulting solution was continued to stir at 0° C. and then rt for 2 h. To the reaction solution was added 500 ml of water and the resulted mixture was extracted with EtOAc. The combined organic phase was washed with water twice, 0.5 N HCl solution once, 5% NaHCO$_3$ solution once and water once. The organic phase was dried (Na$_2$SO$_4$) and evaporated under high vacuum to give 4.87 g (63%) of the compound 116 as a white oil. The compound was used to prepare compound 118 without further purification; $^1H$ NMR (CDCl$_3$) δ1.33–1.37 (m, 2H), 1.45–1.51 (m, 4H), 2.41 (s, 3H), 2.91 (t, 2H), 3.57 (t, 2H), 7.30 (d, 2H), 7.72 (d, 2H); MS (ESI) m/z 280.5 (M+Na)$^+$ ($C_{12}H_{19}NO_3SNa$ requires 280.4).

Compound 118 (Scheme 18). To a solution of compound 116 (1.29 g, 5 mmol), naproxen 1 (1.15 g, 5 mmol) and DMAP (0.12 g, 1 mmol) in CH$_2$Cl$_2$ was added DCC (1.03 g, 5 mmol) at 0° C. The resulting solution was stirred at 0° C. for 2h and then at rt for another 2 h. The solid was filtered off and the solvent was evaporated. The residue was dissolved in EtOAc and filtered to remove more solid. The filtrate was washed with water three times, dried (Na$_2$SO$_4$) and concentrated. The product was purified by flash chromatography on a silica gel column using ethyl ether as an eluent to give 2.06 g (88%) of the compound 118 as a solid; $^1H$ NMR (CDCl$_3$) δ1.13–1.18 (m, 2H), 1.25–1.34 (m, 2H), 1.45–1.51 (m, 2H), 1.55 (d, 3H), 2.40 (s, 3H), 2.77 (q, 2H), 3.81 (q, 1H), 3.90 (s, 3H), 3.96–4.02 (m, 2H), 4.47 (t, 1H, ex D$_2$O), 7.12–7.14 (m, 2H), 7.26 (d, 2H), 7.38 (d, 1H), 7.65–7.70 (m, 5H); MS (ESI) m/z 492.5 (M+Na)$^+$ ($C_{26}H_3NO_5SNa$ requires 492.6).

EXAMPLE 49

Compound 117 (Scheme 18). Compound 117 was prepared by the similar procedure as described above for compound 116 from 6-amino-1-hexanol 114 (3.5 g, 30 mmol) and compound 115 (5.7 g, 30 mmol). The product was purified by flash chromatography on a silica gel column using ethyl ether as an eluent to give 6.5 g (80%) of the compound 117 as a white solid; $^1$H NMR (CDCl$_3$) δ1.26–1.29 (m, 4H), 1.43–1.49 (m, 4H), 2.40 (s, 3H), 2.89 (t, 2H), 3.57 (t, 2H), 7.27 (d, 2H), 7.73 (d, 2H); MS (ESI) m/z 272.4 (M+H)$^+$ (C$_{13}$H$_{22}$NO$_3$S requires 272.4).

Compound 119 (Scheme 18). Compound 119 was prepared by the similar procedure as described above for compound 118 from compound 117 (1.36 g, 5 mmol), naproxen 1 (1.15 g, 5 mmol), DCC (1.03 g, 5 mmol) and DMAP (0.12 g, 1 mmol). The product was purified by flash chromatography on a silica gel column using ethyl ether as an eluent to give 2.04 g (84%) of the compound 119 as a white solid; $^1$H NMR (CDCl$_3$) δ1.11 (m, 4H), 1.23–1.29 (m, 2H), 1.46–1.56 (m, 2H), 1.56 (d, 3H), 2.40 (s, 3H), 2.79 (q, 2H), 3.82 (q, 1H), 3.91 (s, 3H), 3.96–4.05 (m, 2H), 4.43 (t, 1H, ex D$_2$O), 7.11–7.14 (m, 2H), 7.26–7.29 (m, 2H), 7.37–7.39 (q, 1H), 7.64–7.72 (m, 5H); $^{13}$C NMR (CDCl$_3$) δ18.5 21.7, 25.4, 26.1, 28.4, 29.5, 43.1, 45.7, 55.5, 64.6, 105.8, 119.1, 126.1, 126.4, 127.3, 129.1, 129.4, 129.8, 133.8, 136.1, 137.2, 143.5, 157.8, 174.1; MS (ESI) m/z 484.7(M+H)$^+$ (C$_{27}$H$_{34}$NO$_5$S requires 484.6).

The syntheses described in Examples 50 and 51 are outlined in Scheme 19.

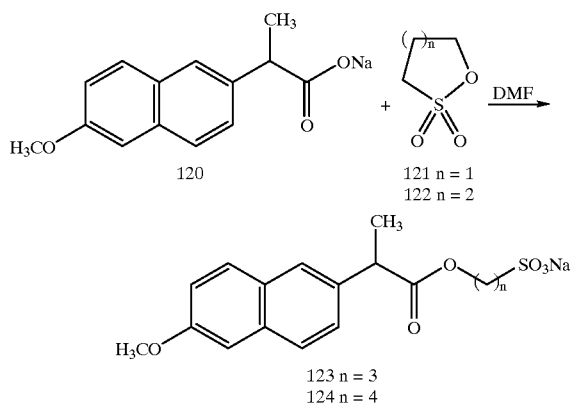

Scheme 19

EXAMPLE 50

Compound 123 (Scheme 19). A mixture of naproxen sodium 120 (2.52 g, 10 mmol) and propanesulton 121 (1.22 g, 10 mmol) in 50 ml of N,N-dimethylformamide (DMF) was stirred at 50–60° C for 30 min. To the reaction solution was added 150 ml of acetone and then stood still for 1 h. Filtration and washing by acetone provided 3.2 g (86%) of the compound 123 as a white powder; $^1$H NMR (D$_2$O) δ1.37 (d, 3H), 1.93–1.97 (m, 2H), 2.74–2.77 (m, 2H), 3.72 (q, 1H), 3.72 (s, 3H), 4.01–4.05 (m, 1H), 4.08–4.11 (m, 1H), 6.97–7.00 (m, 2H), 7.20–7.22 (q, 1H), 7.44 (s, 1H), 7.50 (t, 2H); $^{13}$C NMR (D$_2$O) δ16.7, 23.1, 44.4, 46.9, 54.6, 63.2, 105.4, 117.9, 125.1, 125.5, 126.7, 128.1, 128.7, 132.7, 134.9, 156.3, 176.4; MS (ESI) m/z 397.1 (M+Na)$^+$ (C$_{17}$H$_{19}$Na$_2$O$_5$S requires 397.4).

EXAMPLE 51

Compound 124 (Scheme 19). Compound 124 was prepared by the similar procedure as described above for compound 123 from butanesulton 122 (1.02 ml, 1.36 g, 10 mmol) and naproxen sodium 120 (2.52 g, 10 mmol). After reaction, acetone was added and the solid was filtered and washed with acetone to give 1.3 g (34%) of the compound 124 as a white powder; $^1$H NMR (D$_2$O) δ1.22 (d, 3H), 1.34–1.38 (m, 2H), 1.50–1.56 (m, 2H), 2.65 (t, 2H), 3.44 (s, 3H), 3.47 (m, 1H), 3.74–3.77 (m, 1H), 3.83–3.86 (m, 1H), 6.74 (s, 1H), 6.78–6.81 (d, 1H), 7.05 (d, 1H), 7.22–7.29 (m, 3H); MS (ESI) m/z 411.2 (M+Na)$^+$ (C$_{18}$H$_{21}$Na$_2$O$_6$S requires 411.2).

The synthesis described in Example 52 is outlined in Scheme 20.

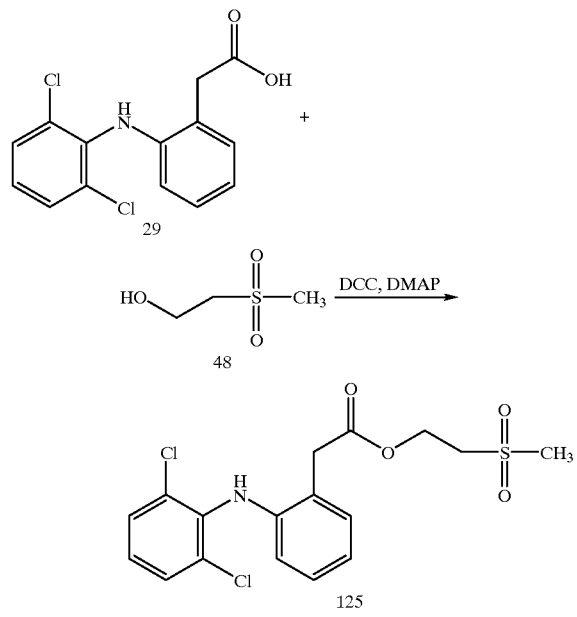

Scheme 20

EXAMPLE 52

Compound 125 (Scheme 20). To a mixture of diclofenac 29 (2.96 g, 10 mmol), methylsulfonylethanol 48 (1.24 g, 10 mmol) and DMAP (0.24 g, 2 mmol) in 50 ml of CH$_2$Cl$_2$ was added DCC (2.06 g, 10 mmol) at 0° C. The resulting mixture was stirred at 0° C. for 2 h. The mixture was filtered and the filtrate was evaporated. The residue was washed with methanol to give 1.83 g (92%) of the compound 125 as a white powder; $^1$H NMR (CDCl$_3$) δ2.75 (s, 3H), 3.30 (t, 2H), 3.84 (s, 2H), 4.58 (t, 2H), 6.51 (d, 1H), 6.93 (t, 1H), 7.00 (t, 1H), 7.12 (t, 1H), 7.19 (d, 1H), 7.34 (d, 2H); $^{13}$C NMR (CDCl$_3$) δ38.5, 42.1 54.0,58.8, 118.3, 122.2, 123.4, 124.7, 128.6, 129.1, 129.9, 131.1, 137.6, 142.8, 171.5; MS (ESI) m/z 402.4 M$^+$ (C$_{17}$H$_{17}$Cl$_2$NO$_4$S requires 402.4).

The synthesis described in Example 53 is outlined in Scheme 21.

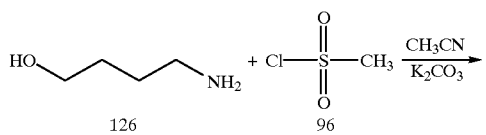

Scheme 21

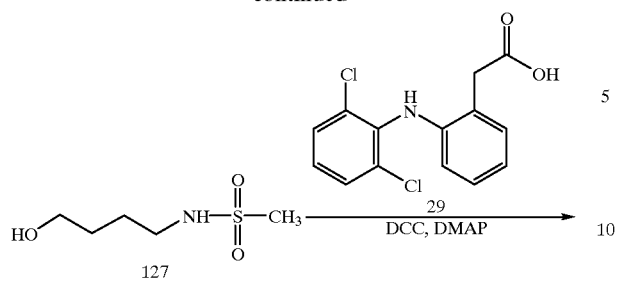

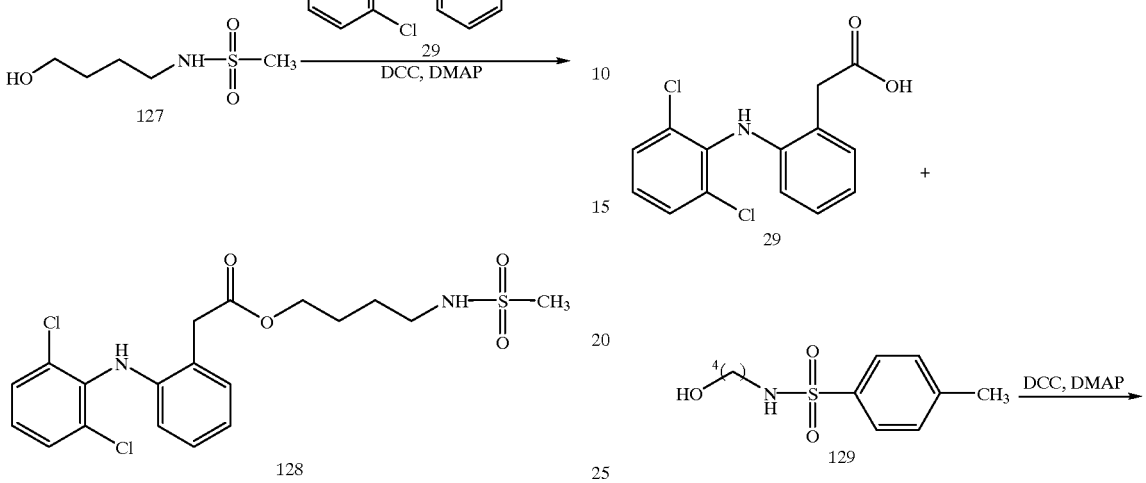

EXAMPLE 53

Compound 127 (Scheme 21). To a mixture of 4-amino-1-butanol 126 (9 g, 100 mmol) and $K_2CO_3$ (34.5 g, 250 mmol, 2.5 equiv) in 200 ml of acetonitril was added dropwise methanesulfonyl chloride 96 (6.95 ml, 10.3 g, 90 mmol, 3 equiv) in 100 ml of $CH_3CN$ at 0° C. The resulting solution was stirred at 0° C. for 1 h. The reaction mixture was filtered and the solvent was evaporated. The residue was purified by flash chromatography on a silica gel column using 50:1 $CH_2Cl_2$-MeOH as an eluent to give 3.45 g (21%) of the compound 127 as a white powder; $^1H$ NMR ($CDCl_3$) δ1.42–1.49 (m, 4H), 2.89 (s, 3H), 2.91 (q, 2H), 3.39 (q, 2H), 4.39 (t, 2H), 6.91 (t, 1H, ex $D_2O$); $^{13}C$ NMR ($CDCl_3$) δ26.1, 29.6, 42.4, 60.2, one peak is covered by DMSO-$d_6$ peaks; MS (ESI) m/z 190.1 (M+Na)$^+$ ($C_5H_{13}NO_3SNa$ requires 190.2).

Compound 128 (Scheme 21). Compound 128 was prepared by the similar procedure as described above for the compound 125 from diclofenac 29 (1.48 g, 5 mmol), compound 127 (0.83 g, 5 mmol), DCC (1.03 g, 5 mmol) and DMAP (0.12 g, 1 mmol). The product was purified by recrystallization from $CH_2Cl_2$-hexanes to give 1.5 g (67%) of the compound 128 as a white powder; $^1H$ NMR ($CDCl_3$) δ1.57–1.62 (m, 2H), 1.70–1.74 (m, 2H), 2.91 (s, 3H), 3.11 (q, 2H), 3.80 (s, 2H), 4.17 (t, 2H), 4.44 (t, 1H, ex $D_2O$), 6.54 (d, 1H), 6.87 (bs, 1H, ex $D_2O$), 6.94–7.00 (m, 2H), 7.12 (t, 1H), 7.23 (t, 1H), 7.34 (d, 2H); $^{13}C$ NMR ($CDCl_3$) δ25.8, 26.8, 38.8, 40.5, 42.9, 64.7, 118.4, 122.2, 124.3, 124.4, 128.2, 129.1, 129.7, 131.1, 137.9, 142.9, 172.5; MS (ESI) m/z 445.3 M$^+$ ($C_{19}H_{22}Cl_2N_2O_4S$ requires 445.3).

The synthesis described in Example 54 is outlined in Scheme 22.

Scheme 22

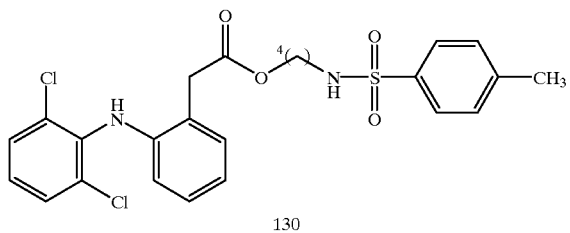

EXAMPLE 54

Compound 130 (Scheme 22). Compound 130 was prepared by the similar procedure as described above for the compound 125 from diclofenac 29 (1.48 g, 5 mmol), compound 129 (1.22 g, 5 mmol), DCC (1.03 g, 5 mmol) and DMAP (0.12 g, 1 mmol). The product was purified by recrystallization from $CH_2Cl_2$-hexanes to give 1.3 g (50%) of the compound 130 as a white powder; $^1H$ NMR ($CDCl_3$) δ1.47–1.51 (m, 2H), 1.62–1.66 (m, 2H), 2.41 (s, 3H), 2.90–2.94 (q, 2H), 3.77 (s, 2H), 4.09(t, 2H), 4.34 (t, 1H, ex $D_2O$), 6.53 (d, 1H), 6.86 (bs, 1H, ex $D_2O$), 6.93–7.00 (m, 2H), 7.11(m, 1H), 7.20 (d, 1H), 7.28–7.35 (m, 4H), 7.72 (d, 2H); MS (ESI) m/z 544.2 (M+Na)$^+$ ($C_{25}H_{26}Cl_2N_2O_4SNa$ requires 544.4).

The synthesis described in Example 55 is outlined in Scheme 23.

Scheme 23

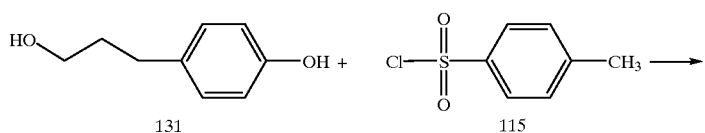

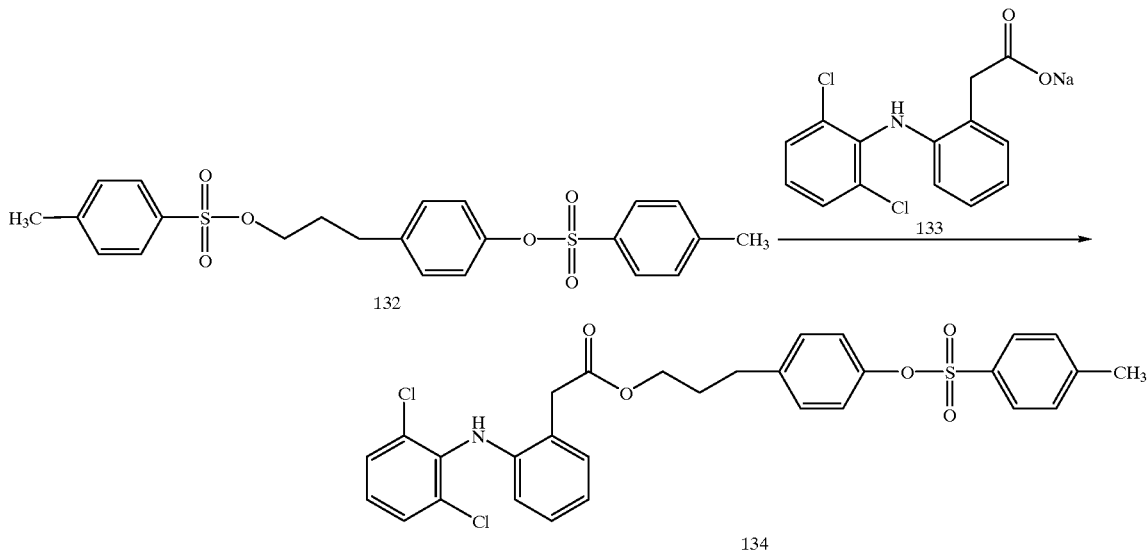

EXAMPLE 55

Compound 132 (Scheme 23). To a solution of 4-(hydroxyphenyl)-1-propanol 131 (3.04 g, 20 mmol) in 20 ml of pyridine was added compound 115 (15.2 g, 80 mmol, 4 equiv) at 0° C. The resulting solution was stirred at 0° C. for 2 h and then at rt for another 2 h. To the reaction solution was added 200 ml of water. The resulting mixture was extracted with EtOAc twice. The combined organic phase was washed with water five times, 0.5N HCl solution once, 5% $Na_2CO_3$ solution once and water again. The organic phase was dried ($Na_2SO_4$) and the solvent was evaporated to give 7.9 g (86%) of the compound 132 as a pale yellow oil; $^1$H NMR ($CDCl_3$) δ1.90 (m, 2H), 2.4 (s, 6H), 2.6 (t, 2H), 3.98 (t, 2H), 6.82–6.84 (q, 2H), 6.97 (d, 2H), 7.29–7.34 (q, 4H), 7.68 (d, 2H), 7.76 (d, 2H); MS (ESI) m/z 483.3 $(M+Na)^+$ ($C_{23}H_{24}O_4S_2Na$ requires 483.5).

Compound 134 (Scheme 23). A mixture of diclofenac sodium 133 (1.59 g, 5 mmol), compound 132 (2.3 g, 5 mmol) and $K_2CO_3$ (1.38 g, 10 mmol) was stirred at rt for 22 h. After reaction, water and EtOAc were added and the two layers were separated. The organic phase was washed with water four times, dried ($Na_2SO_4$) and concentrated. The residue was purified by flash chromatography on a silica gel column using 5:1 $CH_2Cl_2$-hexanes as an eluent to give 1.7 g (59%) of the compound 134 as a pale yellow oil; $^1$H NMR ($CDCl_3$) δ1.90–1.96 (m, 2H), 2.43 (s, 3H), 2.60 (t, 2H), 3.79 (s, 3H), 4.12 (t, 2H), 6.55 (d, 1H), 6.87 (t, 3H), 6.94–7.01 (m, 4H), 7.09–7.13 (m, 1H), 7.22–7.35 (m, 5H), 7.69 (d, 2H); $^{13}$C NMR ($CDCl_3$) δ22.1, 30.4, 31.8, 32.5, 64.8, 118.7, 122.5, 122.7, 124.5, 124.8, 128.5, 128.9, 129.3, 129.9, 129.95, 130.1, 131.2, 132.9, 138.2, 140.5, 143.1, 145.7, 148.4, 172.7; MS (ESI) m/z 584.3 $M^+$ ($C_{30}H_{27}Cl_2NO_5S$ requires 584.5$^1$).

EXAMPLE 56

Reduced Numbers of Intestinal Ulcers in Rat Acute and Subacute Enteropathy Models by the Invention Modified NSAID (Compound 19)! a Prodrug of Naproxen NSAIDs are important drugs used to treat acute and chronic inflammation as well as pain and fever. The major limitation to NSAID use is the occurrence of gastrointestinal ulcers and erosions. These side effects are produced by a combination of local and systemic effects. Attempts have been made to circumvent the local side effects of NSAIDs by making them as prodrugs, which will bypass the stomach, but so far this has not been clearly successful. It is demonstrated here that the invention modified NSAIDs substantially reduce GI toxicity, while exhibiting dose equivalent efficacy in anti-inflammation activity in both acute and chronic inflammation animal models.

Sprague-Dawley rats (male, 150–200 g), were orally dosed once daily for either 3 days (acute model) or 14 days (subacute model). Twenty-four hours after the last dose, the rats were injected i.v. with Evans Blue (5 ml/kg, 10 mg/ml) to stain the ulcers. Ten to twenty minutes later the animals were sacrificed by CO2 inhalation and the intestines removed, opened lengthwise and the contents removed. The long dimensions of all ulcers were measured using a ruler and summed to give a total ulcer score.

Figure 2:
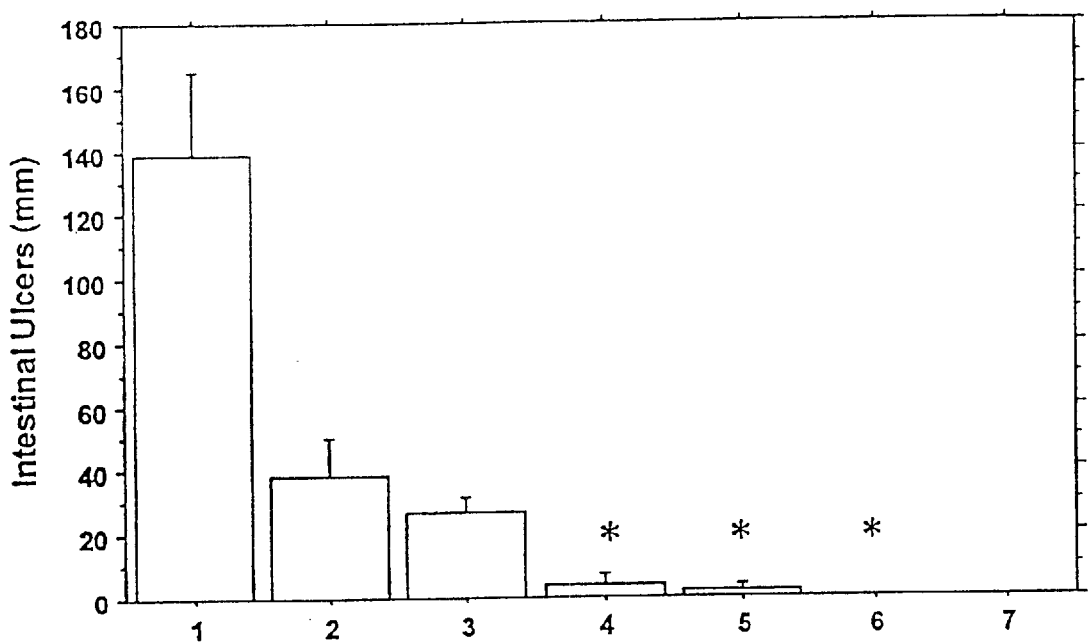
FIG. 2 illustrates the total length of intestinal ulcers measured after 14 daily doses of NSAID in unfasted male Sprague-Dawley rats (150–200 g) treated with vehicle (bar 7), three doses of naproxen (bar 1:50 mg/kg, bar 2:45 mg/kg, bar 3:40 mg/kg), or three equimolar doses of invention composition (compound 19) (bars 4–6). *$P<0.05$ by unpaired t-test vs. corresponding dose of naproxen.

In the acute model (FIG. 1), ulceration after dosing with an invention modified NSAID (compound 19) was 15% of that seen with an equimolar dose of naproxen. PEG had no ulcerogenic effect. In the subacute model (FIG. 2), ulceration was less than 5% of that seen with a corresponding dose of naproxen at all three doses used. Again, PEG had no effect. These results suggest that invention modified NSAIDs are much less ulcerogenic than naproxen.

EXAMPLE 57

Reduction of Chronic Hindlimb Inflammation in the Rat Adjuvant Arthritis Model by the Invention Modified NSAID (Compound 19), a Prodrug of Naproxen NSAIDs are useful in the treatment of both chronic and acute inflammatory conditions. Efficacy in chronic inflammation can be estimated using the rat adjuvant arthritis model. In this model Lewis male rats (175–250 g) are injected intradermally in the footpad with M. tuberculosis powder suspended in mineral oil at 5 mg/ml. Progressive swelling of the uninjected paw and ankle joint between days 5 and 15 is measured by plethysmometry.

Figure 3:
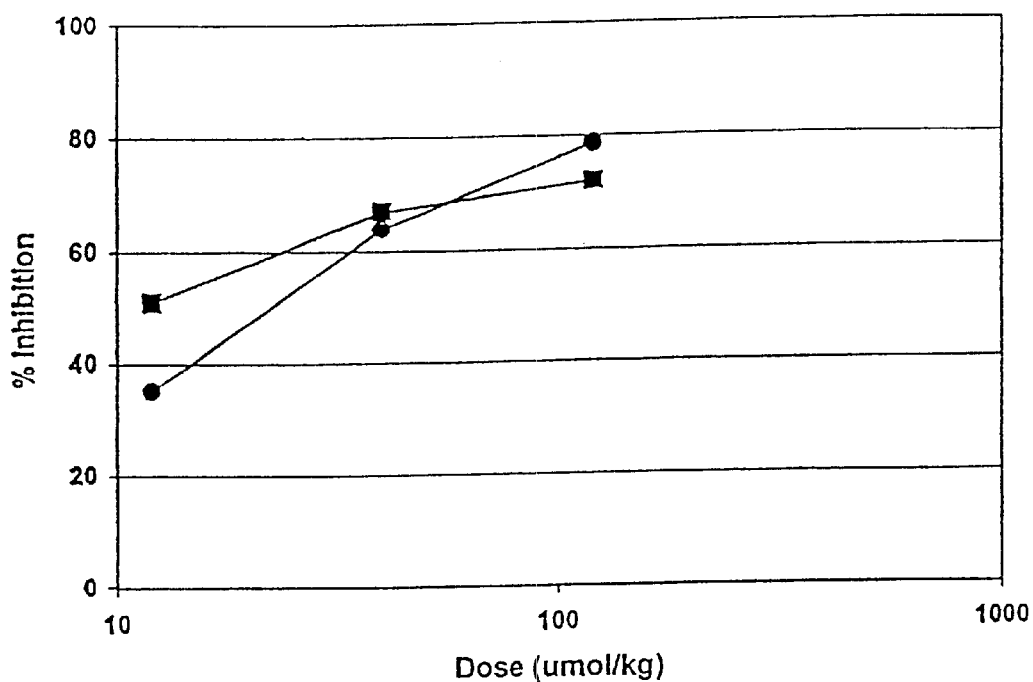
FIG. 3 illustrates the inhibition of paw volume increases in the uninjected feet of Lewis male rats in which arthritis was induced by intradermal injection of adjuvant into the footpad. Rats were injected on day 0 and treated once daily from days 8 to 15 with vehicle, naproxen (10 mg/kg), or invention composition (compound 19) at equivalent dose. Paw volumes were measured with a Plethysmometer on days 5 and 15. Closed circles=naproxen; squares=invention composition.
Figure 4:
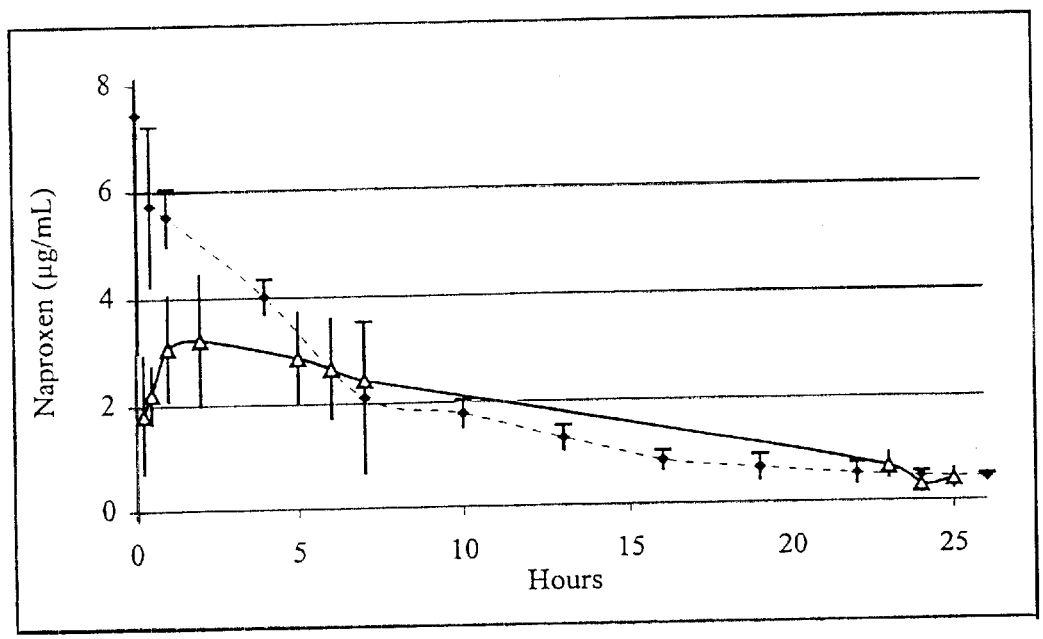
FIG. 4 compares naproxen plasma concentration-time profiles (n=4, mean±s.d.) after oral administration of naproxen (darkened circles) at 2 mg/kg and modified naproxen (open triangles) at an equivalent dose of 2 mg/kg with respect to naproxen in rats. At predetermined times, blood samples were collected and centrifuged to obtain the plasma samples. The plasma naproxen levels were measured by HPLC with a UV detection system.

Rats were dosed daily by oral gavage with 5 ml/kg of naproxen at 3 to 30 mg/kg in phosphate buffered saline (PBS) and with equimolar doses of an invention modified NSAID at 1 ml/kg in PEG 300. The results (FIG. 3) show that the invention modified NSAID resulted in antiinflammatory effects comparable to those of naproxen in this model.

EXAMPLE 58

Reduction of Acute Hindlimb Inflammation in the Rat Carrageenan-induced Hindlimb Edema Model by the Invention Modified NSAID (Compound 19), a Prodrug of Naproxen Efficacy of NSAIDs in acute inflammation can be estimated by using intraplantar injection of carrageenan in the rat. Sprague-Dawley rats (200–250 g male) are injected intradermally in the footpad with 50 (1 of a 1% carrageenan solution in PBS. Swelling of the injected paw is measured 3 & 4 hours later, using a plethysmometer.

Pretreatment with oral naproxen one hour before the carrageenan injection at 10 mg/kg resulted in an approximately 50% reduction in swelling at both time points (Table 1). An equimolar dose of an invention modified NSAID reduced inflammation to the same degree at both time points. These results suggest that invention modified NSAIDs are comparable in effect to naproxen at 10 mg/kg.

TABLE 1

Effects of naproxen and the invention modified NSAID (compound 19) on paw volume increase in carrageenan-induced inflammation in rats.

| Treatment | 4 Hours | 5 Hours |
| --- | --- | --- |
| Vehicle | 0.73 ± 0.10 | 0.85 ± 0.10 |
| Naproxen (1 mg/kg) | 0.63 ± 0.07 | 0.75 ± 0.08 |
| Naproxen (10 mg/kg) | 0.32 ± 0.05* | 0.39 ± 0.07* |
| Compound 19 (1.75 mg/kg) | 0.78 ± 0.04 | 0.93 ± 0.04 |
| Compound 19 (17.5 mg/kg) | 0.34 ± 0.06* | 0.40 ± 0.06* |

P < 0.05 vs Vehicle by unpaired t-test.

Invention modified NSAIDs are seen to have antiinflammatory activity similar to naproxen in the chronic adjuvant arthritis and acute carrageenan hindlimb edema rat models. The tendency to cause intestinal ulcers is reduced substantially invention modified NSAID. Thus, invention modified NSAIDs provide an effective prodrug form of naproxen with reduced intestinal side effects.

EXAMPLE 59

Plasma Pharmacokinetics of Naproxen and the Invention Modified NSAID After Oral Administration in Rats The invention compound (compound 19) is a naproxen prodrug, which is a conjugate of naproxen and tosylate. Oral administration of the invention compound resulted in the release of free naproxen. The pharmacokinetics of naproxen release from the invention modified NSAID and its parent drug, naproxen, was evaluated in rats after oral administration.

The carotid artery of Sprague-Dawley rat (250–350 g, male) was catheterized at least one day before drug administration and flushed with 30% polyvinyl pyrrolidone (PVP) (400 U/mL of heparin) to maintain patency. At predetermined time points (see Table 2), blood samples (250 (L) were collected by unhooking the flushing syringe and letting the blood flow out of the catheter and into the centrifuge tubes. After centrifugation (13,000 rpm, 10 min, 4° C.), the plasma samples were collected and analyzed in the same day.

TABLE 2

Rat group assignment and doses

| Test Article | Group # | Rat # | Dose* (mg/kg) | Sample Time |
| --- | --- | --- | --- | --- |
| Naproxen | 1 | 1, 2, 3, & 4 | Oral (2 mg/kg) | 5 min, 0.5, 1, 4, 7, 10, 13, 16, 19, 22, & 24 hrs |
| Invention Compound 19 | 2 | 5, 6, 7, & 8 | Oral (2 mg/kg) | 15 min, 0.5, 1, 3, 5, 6, 7, 8, 22, 23, & 24 hrs |

*Indicates amount of naproxen in dose.

Aliquot of plasma sample (100 μL) was mixed with 200 μL of acetonitrile. After vortexing and centrifugation (13,000 rpm, 10 min, 4° C.), 200 (L of supernatant was removed and added to 300 (L of a 58:42 mixture of 50 mM phosphate buffer (pH 5.0) and acetonitrile. Following vortexing and centrifugation, 25 L of supernatant was removed and analyzed by HPLC with a UV detection system.

The average plasma concentration at each time point was calculated and utilized in a pharmacokinetic analysis. Non-compartmental pharmacokinetic analysis was carried out using WinNolin (Pharsight, Mountainview, Calif.) to calculate the maximum concentration ($C_{max}$), time to maximum concentration ($T_{max}$), area under the curve from zero to the last time point ($AUC_{last}$), the area under the curve from zero to infinite time ($AUC_{inf}$), and the terminal phase half life (Beta-$t_{1/2}$).

The $AUC_{all}$, $AUC_{INF,\ and\ t1/2}$ of naproxen from naproxen and a modified form of naproxen according to the invention were found to be similar (Table 3). On the other hand, for the invention modified form of neproxen, the $C_{max}$ was lower and the $T_{max}$ longer, compared to naproxen (see Table 3).

TABLE 3

Non-Compartmental Pharmacokinetic Analysis of naproxen and the invention modified form of naproxen according to the (compound 19) after oral administration in rats

| Drug | Dose* (mg/kg) | $C_{max}$ (μg/mL) | $T_{max}$ (hrs) | $AUC_{all}$ (μg*hr/mL) | $AUC_{INF}$ (μg*hr/mL) | $t_{1/2}$ (hrs) | N |
| --- | --- | --- | --- | --- | --- | --- | --- |
| Naproxen | 2 | 7.77 ± 4.13 | 0.5 ± 0.5 | 50 ± 6 | 55 ± 7 | 6.2 ± 0.4 | 4 |
| Invention modified naproxen | 2 | 3.87 ± 1.05 | 6.8 ± 1.5 | 49 ± 10 | 56 ± 14 | 6.8 ± 2.7 | 4 |

*Indicates amount of naproxen in dose.

Following oral naproxen administration, the naproxen plasma levels were at the highest at the first time-point (5 minutes) then declined in a bi-exponential manner. In contrast, after oral administration of a modified form of naproxen according to the invention, the maximum naproxen levels were observed at a much later time ($T_{max}$ of 6.8±1.5 hrs). The similar $AUC_{all}$, $AUC_{INF}$, and $T_{1/2}$ values but lower $C_{max}$ and longer $T_{max}$ values supports the conclusions drawn from the results obtained from pharmacological studies, i.e. that a modified form of naproxen according to the invention conjugate has equivalent pharmacological efficacy and greatly improved gastrointestinal safety profile compared to naproxen.

While the invention has been described in detail with reference to certain preferred embodiments thereof, it will be understood that modifications and variations are within the spirit and scope of that which is described and claimed.

What is claimed is:

1. A method for the alleviation of side effects induced by the administration of a non-steroidal anti-inflammatory drug (NSAID) to a subject, said method comprising chemically modifying said NSAID prior to administration to a subject, wherein said NSAID is chemically modified by covalent attachment thereto of a sulfur-containing functional group to give a structure:

X-L-Z wherein:
X=a non-steroidal anti-inflammatory drug (NSAID),
L=a covalent bond, a linker, or a spacer,
Z=a sulfur-containing functional group containing a substituted or unsubstituted hydrocarbyl moiety, wherein the sulfur-containing functional group is sulfoxide, sulfonate, reverse sulfonate, sulfonamide, reverse sulfonamide, sulfone, sulfinate, or reverse sulfinate, wherein said chemically modified NSAID
a) reduces the maximum concentration ($C_{max}$) relative to the unmodified NSAID and
b) maintains a therapeutically effective concentration of said NSAID in plasma upon administration to said subject.

2. The method according to claim 1, wherein the $C_{max}$ is reduced relative to the unmodified NSAID by about 10% to 90%.

3. The method according to claim 2, wherein the $C_{max}$ is reduced relative to the unmodified NSAID by about 20% to 80%.

4. The method according to claim 3, wherein the $C_{max}$ is reduced relative to the unmodified NSAID by about 40% to 70%.

5. The method according to claim 1, wherein the NSAID is chemically modified so as to achieve a $C_{max}$ upon administration at or below the $IC_{50}$ value for COX 1 enzyme.

6. The method according to claim 1, wherein the NSAID is acetaminophen, aspirin, ibuprofen, choline magnesium salicylate, choline salicylate, diclofenac, diflunisal, etodolac, fenprofen calcium, flurobiprofen, indomethacin, ketoprofen, carprofen, indoprofen, ketorolac tromethamine, magnesium salicylate, meclofenamate sodium, mefenamic acid, oxaprozin, piroxicam, sodium salicylate, sulindac, tolmetin, meloxicam, nabumetone, naproxen, lornoxicam, nimesulide, indoprofen, remifenzone, salsalate, tiaprofenic acid, or flosulide.

7. The method according to claim 6 wherein said NSAID is naproxen, aspirin, ibuprofen, flurbiprofen, indomethacin, ketoprofen, carprofen, or etodolac.

8. The method according to claim 1 wherein the NSAID is administered to a subject for the treatment of a pathological condition.

9. The method according to claim 8 wherein said pathological condition is inflammation.

10. The method according to claim 8 wherein the NSAID is administered to a subject for the treatment of anelgesia.

11. A method for alleviating the systemic toxicity of a non-steroidal anti-inflammatory drug (NSAID), said method comprising chemically modifying said NSAID prior to administration to a subject, wherein said NSAID is chemically modified by covalent attachment thereto of a sulfur-containing functional group to give a structure:

X-L-Z wherein:
X=a non-steroidal anti-inflammatory drug (NSAID),
L=a convalent bond, a linker, or a spacer,
Z=a sulfur-containing functional group containing a substituted or unsubstituted hydrocarbyl moiety, wherein the sulfur-containing functional group is sulfoxide, sulfonate, reverse sulfonate, sulfonamide, reverse sulfonamide, sulfone, sulfinate, or reverse sulfinate, wherein said chemically modified NSAID
a) reduces the maximum concentration ($C_{max}$) relative to the unmodified NSAID and
b) maintains a therapeutically effective concentration of said NSAID in plasma upon administration to said subject.

12. A method for reducing the maximum concentration in plasma achieved upon administration of a non-steroidal anti-inflammatory drug (NSAID), said method comprising modifying the NSAID by covalent attachment thereto of a sulfur-containing functional group containing an optionally substituted hydrocarbyl moiety.

13. A method for the controlled release in vivo of a non-steroidal anti-inflammatory drug (NSAID), said method comprising chemically modifying said NSAID by covalent attachment thereto of a sulfur-containing functional group to give a structure:

X-L-Z wherein:
X=a non-steroidal anti-inflammatory drug (NSAID),
L=a convalent bond, a linker, or a spacer,
Z=a sulfur-containing functional group containing a substituted or unsubstituted hydrocarbyl moiety, wherein the sulfur-containing functional group is sulfoxide sulfonate, reverse sulfonate, sulfonamide, reverse sulfonamide, sulfone, sulfinate, or reverse sulfinate, wherein said chemically modified NSAID
reduces the maximum concentration ($C_{max}$) achieved in plasma upon administration to a subject.

14. A method for the treatment of a subject afflicted with a pathological condition, said method comprising administering to said subject a therapeutically effective amount of a chemically modified non-steroid anti-inflammatory drug (NSAID), wherein said chemically modified NSAID is modified by covalent attachment thereto of a sulfur-containing functional group to give a structure:

X-L-Z wherein:
X=a non-steroidal anti-inflammatory drug (NSAID),
L=a convalent bond, a linker, or a spacer,
Z=a sulfur-containing functional group containing a substituted or unsubstituted hydrocarbyl moiety, wherein the sulfur-containing functional group is sulfoxide, sulfonate, reverse sulfonate, sulfonamide, reverse sulfonamide, sulfone, sulfinate, or reverse sulfinate,
wherein the NSAID is effective for treatment of said condition, and
wherein the modified NSAID has a reduced $C_{max}$ value.

15. The method according to claim 14, wherein said pathological condition is septic shock, hemorrhagic shock, anaphylactic shock, toxic shock syndrome, ischemia, cerebral ischemia, administration of cytokines, overexpression of cytokines, ulcers, inflammatory bowel disease, diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, inflammation, burn, infection, hemodialysis, chronic fatigue syndrome, stroke, cancers, cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, urticaria, systemic lupus erythematosus, AIDS, AIDS dementia, chronic neurodegenerative disease, pain, priapism, cystic fibrosis, amyotrophic lateral sclerosis, schizophrenia, depression, premenstrual syndrome, anxiety, addiction, headache, migraine, Huntington's disease, epilepsy, neurodegenerative disorders, gastrointestinal motility disorders, obesity, hyperphagia, solid tumors, malaria, hematologic cancers, myelofibrosis, lung injury, graft-versus-host disease, head injury, CNS trauma, hepatitis, renal failure, liver disease, drug-induced lung injury, myasthenia gravis (MG), ophthalmic diseases, post-angioplasty, restenosis, angina, or coronary artery disease.

16. The method according to claim 15, wherein said pathological condition is arthritis.

17. The method according to claim 16, wherein said arthritis is rheumatoid arthritis or osteoarthritis.

18. The method according to claim 15, wherein said pathological condition is headache.

19. The method according to claim 18, wherein said headache is a migraine.

20. The method according to claim 15, wherein said pathological condition is pre-menstrual syndrome.

21. The method according to claim 15, wherein said pathological condition is pain.

22. The method according to claim 21, wherein said pain is chronic pain.

23. The method according to claim 22, wherein said pain is post-surgical pain.

24. In a method for the administration of a non-steroidal anti-inflammatory drug (NSAID) to a subject for the treatment of a pathological condition, the improvement comprising modifying the NSAID so as to reduce the $C_{max}$ value achieved upon administration to a subject, wherein said NSAID is modified by covalent attachment thereto of a sulfur-containing functional group to give a structure:

X-L-Z wherein:
   X=a non-steroidal anti-inflammatory drug (NSAID),
   L=a covalent bond, a linker, or a spacer,
   Z=a sulfur-containing functional group containing a substituted or unsubstituted hydrocarbyl moiety, wherein the sulfur-containing functional group is sulfoxide, sulfonate, reverse sulfonate, sulfonamide, reverse sulfonamide, sulfone, sulfinate, or reverse sulfinate.

25. A method for the preparation of a modified non-steroidal anti-inflammatory drug (NSAID) having reduced propensity to induce side effects, said method comprising modifying the NSAID so as to reduce the $C_{max}$ value achieved upon administration to a subject, wherein said NSAID is modified by covalent attachment thereto of a sulfur-containing functional group to give a structure:

X-L-Z wherein:
   X=a non-steroidal anti-inflammatory drug (NSAID),
   L=a covalent bond, a linker, or a spacer,
   Z=a sulfur-containing functional group containing a substituted or unsubstituted hydrocarbyl moiety, wherein the sulfur-containing functional group is sulfoxide, sulfonate, reverse sulfonate, sulfonamide, reverse sulfonamide, sulfone, sulfinate, or reverse sulfinate.

* * * * *